(12) United States Patent
Bui

(10) Patent No.: US 7,744,817 B2
(45) Date of Patent: Jun. 29, 2010

(54) MANIFOLD ASSEMBLY

(75) Inventor: Xuan S. Bui, Culver City, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 1027 days.

(21) Appl. No.: 11/349,325

(22) Filed: Feb. 6, 2006

(65) Prior Publication Data

US 2006/0169719 A1 Aug. 3, 2006

Related U.S. Application Data

(63) Continuation-in-part of application No. 10/639,021, filed on Aug. 11, 2003, now Pat. No. 7,501,283.

(60) Provisional application No. 60/652,440, filed on Feb. 11, 2005.

(51) Int. Cl.
*G01N 15/06* (2006.01)

(52) U.S. Cl. .......................... 422/68.1; 422/63; 422/64; 422/65; 422/99; 422/100; 436/174; 436/175; 436/180; 435/7.1

(58) Field of Classification Search ............ 422/63–67, 422/99–101, 68.1; 436/180, 174–175; 435/7.1
See application file for complete search history.

(56) References Cited

U.S. PATENT DOCUMENTS

| | | |
|---|---|---|
| 2,709,025 A | 5/1955 | Scott |
| 2,772,817 A | 12/1956 | Jauch |
| 3,294,290 A | 12/1966 | Erickson et al. |
| 3,904,079 A | 9/1975 | Kross |
| 4,018,363 A | 4/1977 | Cassia |
| 4,025,241 A | 5/1977 | Clemens |
| 4,039,775 A | 8/1977 | Andra |
| 4,099,483 A | 7/1978 | Henderson |
| 4,149,633 A | 4/1979 | Nilson |
| 4,199,558 A | 4/1980 | Henderson |

(Continued)

FOREIGN PATENT DOCUMENTS

CN 2390207 Y 8/2000

(Continued)

OTHER PUBLICATIONS

Office Action for Japanese Application No. 2006-34547 dated Dec. 26, 2008 (7 pages).

(Continued)

*Primary Examiner*—Jyoti Nagpaul
(74) *Attorney, Agent, or Firm*—Blakely Sokoloff Taylor & Zafman LLP

(57) ABSTRACT

A manifold assembly that directs fluid to and from individually selectable sample receiving trays of a tissue processing system includes a manifold, fluid conduits machined in the manifold, and valves that may be selectively configured to provide a direct fluid path to or from a particular tray. The valves are controlled by a controller that positions each valve such that a desired path is created. Pressure is created in supply and/or drain bottles to supply or drain fluid from the trays supported by the manifold assembly. Independently operated heaters are provided on the manifold assembly to heat the trays to desired temperatures. Thermoelectric cooling elements may also provided to cool the heaters and/or trays.

18 Claims, 18 Drawing Sheets

U.S. PATENT DOCUMENTS

| | | |
|---|---|---|
| 4,258,759 A | 3/1981 | Achen |
| 4,356,727 A | 11/1982 | Brown et al. |
| 4,604,964 A | 8/1986 | Gordon et al. |
| 4,667,854 A | 5/1987 | McDermott et al. |
| 4,673,109 A | 6/1987 | Cassia |
| 4,678,752 A | 7/1987 | Thorne et al. |
| 4,731,335 A | 3/1988 | Brigati |
| 4,741,898 A | 5/1988 | Mallik et al. |
| 4,764,342 A | 8/1988 | Kelln et al. |
| 4,790,640 A | 12/1988 | Nason |
| 4,798,311 A | 1/1989 | Workum |
| 4,801,431 A | 1/1989 | Cuomo et al. |
| 4,834,019 A | 5/1989 | Gordon et al. |
| 4,838,457 A | 6/1989 | Swahl et al. |
| 4,846,636 A | 7/1989 | Danby et al. |
| 4,867,347 A | 9/1989 | Wass et al. |
| 4,880,149 A | 11/1989 | Scholefield et al. |
| 4,886,192 A | 12/1989 | Cassia |
| 4,921,136 A | 5/1990 | Roggenburg, Jr. |
| 4,927,061 A | 5/1990 | Leigh et al. |
| 4,946,076 A | 8/1990 | Hackmann et al. |
| 4,955,512 A | 9/1990 | Sharples |
| 4,961,508 A | 10/1990 | Weimer et al. |
| 4,969,581 A | 11/1990 | Seifert et al. |
| 4,972,978 A | 11/1990 | DeLuca |
| 4,974,754 A | 12/1990 | Wirz |
| 4,978,036 A | 12/1990 | Burd |
| 4,985,206 A | 1/1991 | Bowman et al. |
| 5,002,736 A | 3/1991 | Babbitt et al. |
| 5,033,656 A | 7/1991 | Blette et al. |
| 5,035,350 A | 7/1991 | Blette et al. |
| 5,068,091 A | 11/1991 | Toya |
| 5,082,150 A | 1/1992 | Steiner et al. |
| 5,225,325 A | 7/1993 | Miller et al. |
| 5,232,664 A | 8/1993 | Krawzak et al. |
| 5,242,083 A | 9/1993 | Christine et al. |
| 5,244,787 A | 9/1993 | Key et al. |
| 5,252,293 A * | 10/1993 | Drbal et al. ............... 422/101 |
| 5,273,905 A * | 12/1993 | Muller et al. ............ 435/286.5 |
| 5,275,309 A | 1/1994 | Baron et al. |
| 5,316,452 A | 5/1994 | Bogen et al. |
| 5,322,771 A | 6/1994 | Rybski et al. |
| 5,338,358 A | 8/1994 | Mizusawa et al. |
| 5,355,439 A | 10/1994 | Bernstein et al. |
| 5,356,039 A | 10/1994 | Christine et al. |
| 5,418,138 A | 5/1995 | Miller et al. |
| 5,424,036 A | 6/1995 | Ushikubo |
| 5,433,351 A | 7/1995 | Okuyama et al. |
| 5,439,649 A | 8/1995 | Tseung et al. |
| 5,578,452 A | 11/1996 | Shi et al. |
| 5,580,523 A | 12/1996 | Bard |
| 5,595,707 A | 1/1997 | Copeland et al. |
| 5,609,822 A | 3/1997 | Carey et al. |
| 5,626,262 A | 5/1997 | Fitten et al. |
| 5,645,114 A | 7/1997 | Bogen et al. |
| 5,650,327 A | 7/1997 | Copeland et al. |
| 5,654,200 A | 8/1997 | Copeland et al. |
| 5,675,715 A | 10/1997 | Bernstein et al. |
| 5,700,346 A | 12/1997 | Edwards |
| 5,810,204 A | 9/1998 | Devlin et al. |
| 5,839,091 A | 11/1998 | Rhett et al. |
| 5,843,700 A | 12/1998 | Kerrod et al. |
| 5,846,396 A | 12/1998 | Zanzucchi et al. |
| 5,855,302 A | 1/1999 | Fisscher |
| 5,857,595 A | 1/1999 | Nilson |
| 5,885,530 A | 3/1999 | Babson et al. |
| 5,947,167 A | 9/1999 | Bogen et al. |
| 5,948,359 A | 9/1999 | Kalra et al. |
| 5,950,874 A | 9/1999 | Sindoni |
| 5,950,878 A | 9/1999 | Wade et al. |
| 5,954,167 A | 9/1999 | Richardson et al. |
| 5,964,454 A | 10/1999 | Volpel |
| 5,965,454 A | 10/1999 | Farmilo et al. |
| 5,968,731 A | 10/1999 | Layne et al. |
| 5,971,223 A | 10/1999 | Fisscher |
| 6,001,309 A | 12/1999 | Gamble et al. |
| 6,045,759 A | 4/2000 | Ford et al. |
| 6,076,583 A | 6/2000 | Edwards |
| 6,092,695 A | 7/2000 | Loeffler |
| 6,093,574 A | 7/2000 | Druyor-Sanchez et al. |
| 6,096,271 A | 8/2000 | Bogen et al. |
| 6,180,061 B1 | 1/2001 | Bogen et al. |
| 6,183,693 B1 | 2/2001 | Bogen et al. |
| 6,189,740 B1 | 2/2001 | Wade et al. |
| 6,192,945 B1 | 2/2001 | Ford et al. |
| 6,216,916 B1 | 4/2001 | Maddox et al. |
| 6,238,910 B1 | 5/2001 | Custance et al. |
| 6,244,474 B1 | 6/2001 | Loeffler |
| 6,259,956 B1 | 7/2001 | Myers et al. |
| 6,273,298 B1 | 8/2001 | Post |
| 6,296,809 B1 | 10/2001 | Richards et al. |
| 6,335,166 B1 | 1/2002 | Ammann et al. |
| 6,343,716 B1 | 2/2002 | Baudin et al. |
| 6,349,264 B1 | 2/2002 | Rhett et al. |
| 6,352,861 B1 | 3/2002 | Copeland et al. |
| 6,387,326 B1 | 5/2002 | Edwards et al. |
| 6,415,961 B2 | 7/2002 | Bonningue |
| 6,416,713 B1 | 7/2002 | Ford et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,516,620 B2 | 2/2003 | Lang |
| 6,540,117 B2 | 4/2003 | Powling |
| 6,541,261 B1 | 4/2003 | Bogen et al. |
| 6,543,652 B1 | 4/2003 | Kelder et al. |
| 6,544,798 B1 | 4/2003 | Christensen et al. |
| 6,553,145 B1 | 4/2003 | Kang et al. |
| 6,580,056 B1 | 6/2003 | Tacha |
| 6,582,962 B1 | 6/2003 | Richards et al. |
| 6,594,537 B1 | 7/2003 | Bernstein et al. |
| 6,605,213 B1 | 8/2003 | Ammann et al. |
| 6,607,103 B2 | 8/2003 | Gerenraich et al. |
| 6,632,598 B1 | 10/2003 | Zhang et al. |
| 6,635,225 B1 | 10/2003 | Thiem et al. |
| 6,673,620 B1 | 1/2004 | Loeffler et al. |
| 6,729,502 B2 | 5/2004 | Lewis et al. |
| 6,735,531 B2 | 5/2004 | Rhett et al. |
| 6,746,851 B1 | 6/2004 | Tseung et al. |
| 6,758,360 B2 | 7/2004 | Van Giezen et al. |
| 6,783,733 B2 | 8/2004 | Bogen et al. |
| 6,827,900 B2 | 12/2004 | Thiem et al. |
| 6,827,901 B2 | 12/2004 | Copeland et al. |
| 6,855,552 B2 | 2/2005 | Towne et al. |
| 6,855,559 B1 | 2/2005 | Christensen et al. |
| 6,899,283 B2 | 5/2005 | Ohnishi et al. |
| 6,943,029 B2 | 9/2005 | Copeland et al. |
| 6,945,128 B2 | 9/2005 | Ford et al. |
| 6,991,934 B2 | 1/2006 | Walton et al. |
| 6,998,270 B2 | 2/2006 | Tseung et al. |
| 7,007,824 B2 | 3/2006 | Danby et al. |
| 7,070,951 B2 | 7/2006 | Zhang et al. |
| 7,118,918 B2 | 10/2006 | Copeland et al. |
| 7,201,295 B1 | 4/2007 | Sitzberger |
| 7,217,392 B2 | 5/2007 | Bogen et al. |
| 7,220,589 B2 | 5/2007 | Richards et al. |
| 7,226,788 B2 | 6/2007 | De La Torre-Bueno |
| 7,264,142 B2 | 9/2007 | Py |
| 7,270,785 B1 | 9/2007 | Lemme et al. |
| 7,278,554 B2 | 10/2007 | Armstrong |
| 7,303,725 B2 | 12/2007 | Reinhardt et al. |
| 7,314,238 B2 | 1/2008 | Robert |
| 7,323,491 B2 | 1/2008 | Lohray et al. |
| 7,338,803 B2 | 3/2008 | Mizzer et al. |
| 7,435,383 B2 | 10/2008 | Tseung et al. |

| | | | |
|---|---|---|---|
| 7,468,161 B2 | 12/2008 | Reinhardt et al. | |
| 7,470,541 B2 | 12/2008 | Copeland et al. | |
| 2001/0044603 A1 | 11/2001 | Harrold | |
| 2002/0013194 A1 | 1/2002 | Kitano et al. | |
| 2002/0079318 A1 | 6/2002 | Wurzinger | |
| 2002/0114733 A1 | 8/2002 | Copeland et al. | |
| 2003/0100043 A1 | 5/2003 | Kalra et al. | |
| 2003/0157545 A1 | 8/2003 | Jevons et al. | |
| 2003/0203493 A1 | 10/2003 | Lemme et al. | |
| 2004/0033163 A1 | 2/2004 | Tseung et al. | |
| 2004/0091395 A1 | 5/2004 | Ward et al. | |
| 2004/0120862 A1 | 6/2004 | Lang et al. | |
| 2004/0191128 A1 | 9/2004 | Bogen et al. | |
| 2004/0197230 A1 | 10/2004 | Lemme et al. | |
| 2004/0266015 A1 | 12/2004 | Favuzzi et al. | |
| 2005/0019902 A1 | 1/2005 | Mathies et al. | |
| 2005/0035156 A1 | 2/2005 | Hersch et al. | |
| 2005/0064535 A1 | 3/2005 | Favuzzi et al. | |
| 2005/0135972 A1 | 6/2005 | Lemme et al. | |
| 2005/0150911 A1 | 7/2005 | Bach | |
| 2005/0153453 A1 | 7/2005 | Copeland et al. | |
| 2005/0164374 A1 | 7/2005 | Kram | |
| 2005/0186114 A1 | 8/2005 | Reinhardt et al. | |
| 2005/0191214 A1 | 9/2005 | Tseung et al. | |
| 2005/0281711 A1 | 12/2005 | Testa et al. | |
| 2006/0019332 A1 | 1/2006 | Zhang et al. | |
| 2006/0040341 A1 | 2/2006 | Bland et al. | |
| 2006/0045806 A1 | 3/2006 | Winther et al. | |
| 2006/0063265 A1 | 3/2006 | Welcher et al. | |
| 2006/0088928 A1 | 4/2006 | Sweet et al. | |
| 2006/0088940 A1 | 4/2006 | Feingold et al. | |
| 2006/0105359 A1 | 5/2006 | Favuzzi et al. | |
| 2006/0120921 A1 | 6/2006 | Elliot et al. | |
| 2006/0127283 A1 | 6/2006 | Tseung et al. | |
| 2006/0134793 A1 | 6/2006 | Key et al. | |
| 2006/0147351 A1 | 7/2006 | Falb et al. | |
| 2006/0148063 A1 | 7/2006 | Fauzzi et al. | |
| 2006/0190185 A1 | 8/2006 | Ford et al. | |
| 2006/0191952 A1 | 8/2006 | Kalra et al. | |
| 2006/0252025 A1 | 11/2006 | Nitta et al. | |
| 2006/0263268 A9 | 11/2006 | Tseung et al. | |
| 2006/0265133 A1 | 11/2006 | Cocks et al. | |
| 2006/0269985 A1 | 11/2006 | Kitayama | |
| 2007/0010912 A1 | 1/2007 | Feingold et al. | |
| 2007/0038491 A1 | 2/2007 | Samuhel et al. | |
| 2008/0254503 A1 | 10/2008 | Ljungmann et al. | |
| 2008/0286753 A1 | 11/2008 | Erickson et al. | |

FOREIGN PATENT DOCUMENTS

| | | |
|---|---|---|
| DE | 3902476 | 8/1990 |
| EP | 0185330 | 6/1986 |
| EP | 0557871 | 9/1993 |
| EP | 1028320 | 8/2000 |
| GB | 2037255 | 7/1980 |
| JP | 6-510860 | 12/1994 |
| JP | 9-503060 | 3/1997 |
| JP | 10-501167 | 2/1998 |
| JP | 2000167318 | 6/2000 |
| JP | 2001-509727 | 7/2001 |
| JP | 2001-512823 | 8/2001 |
| JP | 2001-522033 | 11/2001 |
| JP | 2002-522065 | 7/2002 |
| JP | 2003-057246 | 2/2003 |
| JP | 2004-533605 | 11/2004 |
| WO | WO 95/08774 | 3/1995 |
| WO | WO 95/26796 | 10/1995 |
| WO | WO 96/39260 | 12/1996 |
| WO | WO 99/08090 | 2/1999 |
| WO | WO 99/22867 | 5/1999 |
| WO | WO 00/09650 | 2/2000 |
| WO | WO 00/12994 | 3/2000 |
| WO | WO 01/41918 | 6/2001 |
| WO | WO 02/072264 A1 | 9/2002 |
| WO | WO 03/054553 | 7/2003 |
| WO | WO 03/091710 | 11/2003 |
| WO | WO 03/106033 | 12/2003 |
| WO | WO 2004/059288 | 7/2004 |
| WO | WO 2004/074847 | 9/2004 |
| WO | WO 2005/000731 | 1/2005 |

OTHER PUBLICATIONS

European Search Report for EP Appln No. 06101498.1, mailed Jun. 20, 2006 (6 pages).

European Search Report for EP Appln No. 06101497.3, mailed Jun. 20, 2006 (6 pages).

PCT Search Report for PCT Appln No. PCT/US04/25960, mailed Aug. 8, 2006 (10 pages).

PCT Search Report for PCT Appln No. PCT/US2007/012400, mailed Nov. 16, 2007 (13 pages).

Zhang, Guangrong, et al., "Deparaffinization compositions and methods for their use," Reissue U.S. Appl. No. 11/250,142, filed Oct. 13, 2005.

Shi, Shan-Rong, et al., "Enhancement of immunochemical staining in aldehyde-fixed tissue," Reissue U.S. Appl. No. 11/249,180, filed Oct. 11, 2005.

Office Action for Chinese Application No. 200610007366.7 dated May 8, 2009 (21 pages).

* cited by examiner

MANIFOLD ASSEMBLY

This application is a continuation-in-part of co-pending U.S. patent application Ser. No. 10/639,021, filed on Aug. 11, 2003, and entitled "Fluid Dispensing Apparatus", and claims priority to provisional U.S. patent application Ser. No. 60/652,440, entitled "Manifold Assembly", filed on Feb. 11, 2005, both of which hereby are incorporated herein by reference in their entireties.

FIELD OF THE INVENTION

The present invention is directed to an automated tissue processing system and in particular, to a manifold assembly for a tissue processing system.

BACKGROUND OF THE INVENTION

Tissue processors can be operated with varying levels of automation to process human or animal tissue specimens for histology or pathology uses. Various types of chemical reagents can be used at various stages of tissue processing and various systems have been developed for delivering reagents to specimen containing slides. Examples of known reagent delivery systems include small quantity release dispensers, manual pouring into reagent vats, or via bulk containers connected with a processor via tubing.

There are various disadvantages of known systems. For example, manually pouring into, or draining, reagent vats suffers a disadvantage being time consuming and requiring pouring accuracy, decreasing the overall efficiency of the tissue processing system. Another disadvantage is that manually pouring and draining reagents is that it can be sloppy, requiring clean-up of spills and consequential instrument down-time. A further disadvantage is that selecting the correct reagent requires operator attention and accuracy and there is an increased possibility of reagent application errors, decreasing test accuracy and decreasing operational efficiency.

In an automated system, there also are disadvantages. Reagents need to be selected and administered to slides during processing. The reagents frequently need to be delivered via gravity promoted dispensing from above. Such delivery systems require specialized equipment for reagent delivery such as specialized reagent dispensers or drivers or automated pipetting systems. Such systems suffer various drawbacks such as the amount of effort required to set up and dispense the reagents, the possibilities of evaporation during processing or contamination and difficulties in handling minute quantities of large numbers of reagents.

One known slide retaining tray and system for staining tissues is described in U.S. Pat. No. 5,338,358, which is incorporated herein by reference. As illustrated in that system, a platen is provided and various mounting elements are provided to mount a slide on the slide tray. Space for five slides is illustrated. A reaction chamber is provided between a platen surface and slide mounted on the tray. Reagents are introduced into the reaction chamber via drip surfaces and attendant capillary action.

SUMMARY OF THE INVENTION

The present invention alleviates to a great extent the disadvantages of the known automated tissue processing systems by providing a manifold assembly in which fluid conduits are etched directly into the manifold. The manifold is preferably formed of two pieces of corrosion resistant, polymeric material. Each piece of material has matching channels etched therein. According to an embodiment of the present invention, channels are machined into each piece of the manifold. When the pieces are joined together conduits are created with the channels facing each other such that fluid may traverse a length of the manifold. The pieces may be joined by, for example, clamping, binding, welding or other known mechanically fastening technique. One advantage to etching two pieces of material to form a conduit by joining the pieces, is that precise tolerances for the conduit may be achieved.

In another aspect of the present invention, the manifold is provided with a plurality of valves that are individually controlled. The valves may be controlled by a controller that positions each of the valves in such a manner as to create a direct passageway from a supply bottle to a particular tray or from a particular tray to a desired waste bottle.

In an embodiment, the controller receives instructions regarding one or more staining procedures that indicate how tissue samples provided in the trays are to be processed from a central processor. The controller, however, preferably downloads these instruction from the central processor and stores the instructions in a local storage. This enables the automated tissue processing system to operate independently of the central processor.

In an embodiment, fluids and/or reagents are introduced, and/or evacuated from below. For example, one or more fluid entry ports, or inlets, may be provided in the manifold and optionally one or more fluid evacuation ports, or outlets, may also be provided in the manifold. Preferably the entry and evacuation ports are at generally opposite ends of the manifold so as to create a fluid flow gradient from one end to the other end of the manifold.

Sample retaining trays, such as microscope slide retaining trays, having corresponding inlets and outlets may also be provided. With a slide positioned in the tray, a reaction chamber may be formed between the slide and the tray, with a fluid flow gradient from one end to the other. In an embodiment, each of the fluid entry and evacuation ports have plural holes, that are relatively small, so that they act as a screen. Optionally, a screen can be positioned on the ports.

In another aspect of the invention, a central portion of the tray is elevated above a bottom surface of the tray. The space formed between the side walls of the elevated portion, the outer walls of the tray, and the bottom of the tray can retain fluid overflow from the elevated portion. Such fluids can be evacuated via the evacuation port(s).

In another aspect of the invention, the manifold assembly is provided with independently operated heaters to heat each tray provided on the manifold assembly to a desired temperature wherein each desired temperature may be different. Thermoelectric coolers may also be provided to cool the heaters and/or portions of the tray.

These and other features and advantages of the present invention will be appreciated from review of the following detailed description of the invention, along with the accompanying figures in which like reference numerals refer to like parts throughout.

DETAILED DESCRIPTION

In the following paragraphs, the present invention will be described in detail by way of example with reference to the figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 1:
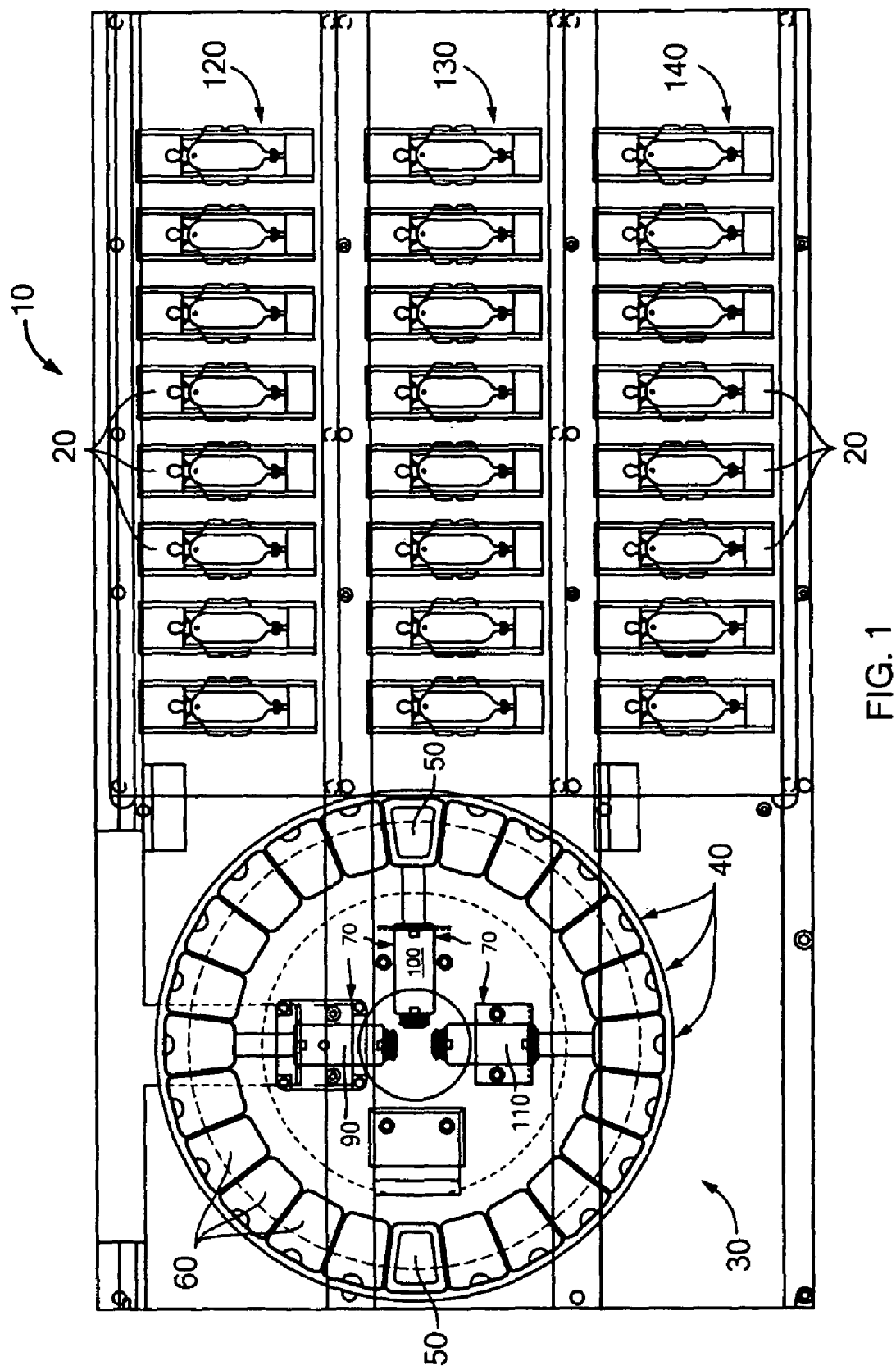
FIG. 1 is a top view of a tissue processing system suitable for use with one or more slide retaining trays in accordance with the present invention.
Figure 2:
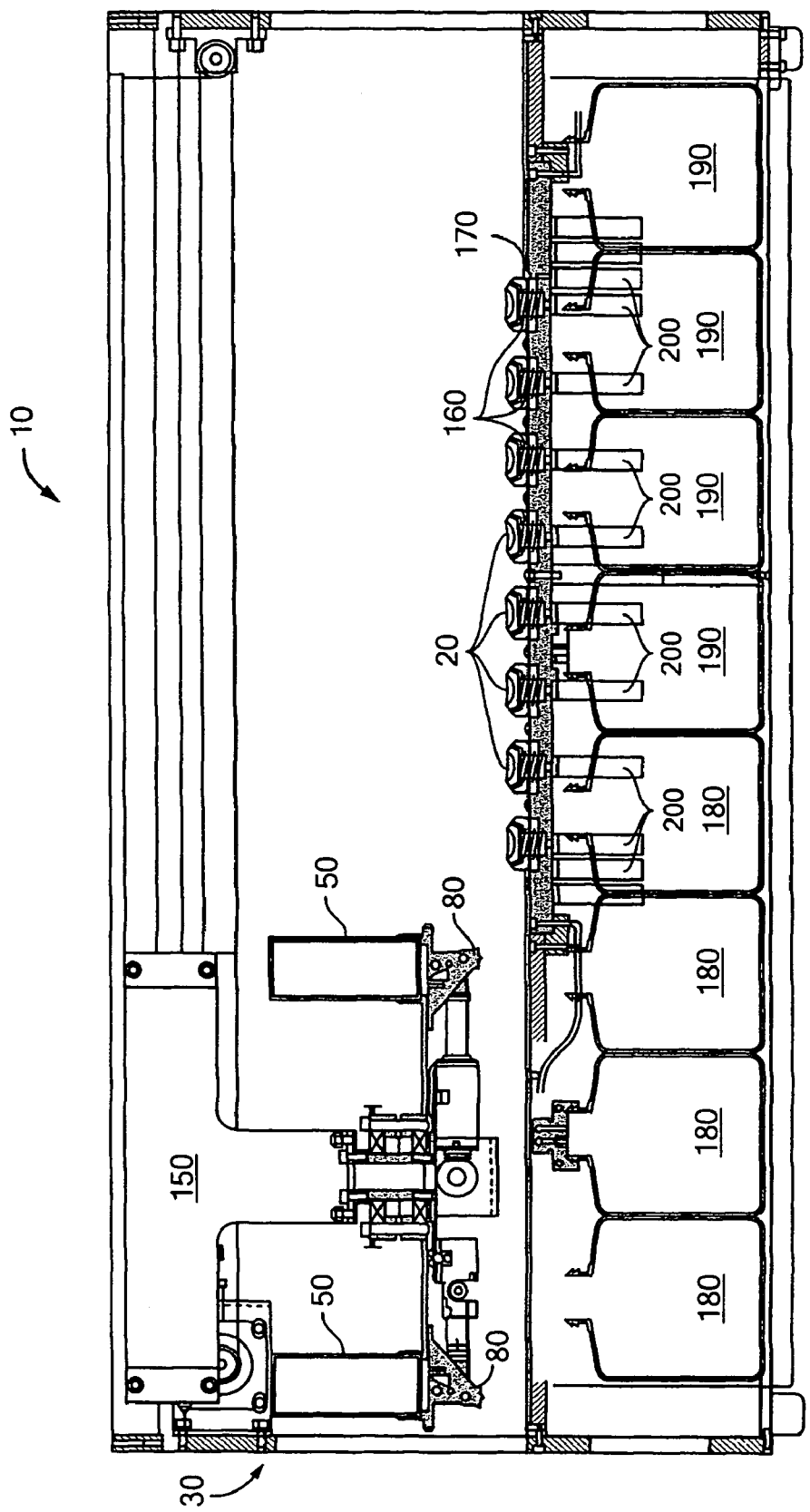
FIG. 2 is a side view of the tissue processing system of FIG. 1.

Referring to FIGS. 1 and 2, a tissue processing system 10 suitable for use with one or more slide, or sample, retaining trays 20 will now be described. The system 10 includes a fluid dispensing apparatus 30 having a plurality of stations 40 at which fluid dispensing cartridges 50 may be mounted. A fluid dispensing apparatus including a multiplicity of fluid dispensing cartridges 50 is described in U.S. patent application Ser. No. 10/639,021, the content of which is hereby incorporated by reference in its entirety. Alternatively, a fluid dispensing system using tubing or pipetting can be used as well, such as described for example in U.S. Pat. No. 5,338,358. The stations 40 include mounting apertures 60 selectively positioning a plurality of fluid dispensing cartridges 50 adjacent to an actuator assembly 70, which is used to trigger the ejection of a desired amount of a fluid, such as a secondary reagent or a de-waxing fluid, from a reagent dispenser 80.

The slide retaining trays 20 are positioned generally beneath fluid dispensing apparatus 30 taking advantage of gravity to deliver fluids from a cartridge 50, onto a drip surface of a desired slide retaining tray 20. Preferably, fluid dispensing apparatus 30 and slide retaining trays 20 are movable with respect to one another so that plural cartridges 50 can be positioned to dispense fluids on any desired tray 20. Any combination of movability of the fluid dispensing apparatus 30 and the slide retaining trays 20 may be selected. For example, both may be movable or only one may be movable and the other stationary. The slide retaining trays 20 may all carry the same type of items, such as slides or alternatively slides and/or other sample containers.

In one example of operation of the tissue processing system 10, the fluid dispensing apparatus 30 is rotated so that individual cartridges 50 are selectively positioned adjacent actuator assembly 70. Alternatively, an actuator assembly may be positioned adjacent to each cartridge 50 such that rotation of the fluid dispensing apparatus 30 is not required. The actuator assembly 70 can be any activation device that triggers the cartridge 50 to emit a controlled amount of fluid. Preferably, the fluid dispensing apparatus may be both translated and rotated with respect to the slide retaining trays 20 so that an individual cartridge 50 can be selectively positioned above any tray 20. Once the cartridge 50 is positioned above a slide retaining tray 20, actuator assembly 70 triggers the cartridge 50 to emit a controlled amount of fluid onto the tray 20.

Actuator assembly 70 optionally includes three actuators 90, 100, 110 used to dispense fluid onto three rows 120, 130, 140 of receiving members, respectively. In operation, actuator 90 is adapted to dispense fluids onto slide retaining trays 20 disposed in row 120, actuator 100 is adapted to dispense fluids onto slide retaining trays 20 disposed in row 130 and actuator 110 is adapted to dispense fluids onto slide retaining trays 20 disposed in row 140. Of course, as will be understood by those of skill in the art, any number of actuators and/or slide retaining trays can be employed without departing from the scope of the present invention.

In a preferred embodiment, the fluid dispensing apparatus 30 is rotatably attached to a support member 150 such that the cartridges 50 can be rotated with respect to the actuator assembly 70. Actuator assembly 70 is fixedly attached to the support member 150, optionally beneath fluid dispensing apparatus 30. Preferably, support member 150 can be translated horizontally such that the cartridges 50 can be both rotated and translated with respect to the trays 20. In this manner, any cartridge 50 can be selectively positioned above any slide retaining tray 20.

Slide retaining trays 20 preferably are mounted on spring loaded heating/cooling pads 160, thereby providing selective and/or independent heating and/or cooling of the slides. Additionally, heating/cooling pads 160 are capable of independently heating the plateau or platen region and the recess region. In one embodiment, each tray has a corresponding heating and/or cooling element 160, maintaining the tray at a particular desired temperature. In an alternative embodiment, there are two or more heating and/or cooling elements for each tray. Preferably, the trays are mounted on a mounting surface 170.

Tissue processing system 10 optionally includes supply bottles 180, drain containers 190 and fluid delivery manifold 200. Supply bottles 180 can be used to hold liquids such as water for rinsing or flushing the gap between the slides and the plateau. Fluid delivery manifold 200 preferably includes valves and switches for directing the flow of fluids supplied through a fluid inlet port and a conduit. In addition, the fluid delivery manifold includes valves and switches for directing the flow of excess fluids and waste material from fluid evacuation ports and conduits into drain, or waste, containers 190.

As shown in FIGS. 1 and 2, a central processor 210 is in communication with the tissue processing system 10. The central processor 210 provides sequences regarding how a particular tissue sample is to be processed. These sequences also provide instructions regarding valve controls such that desired reagents are provided to the particular tissue.

Figure 3:
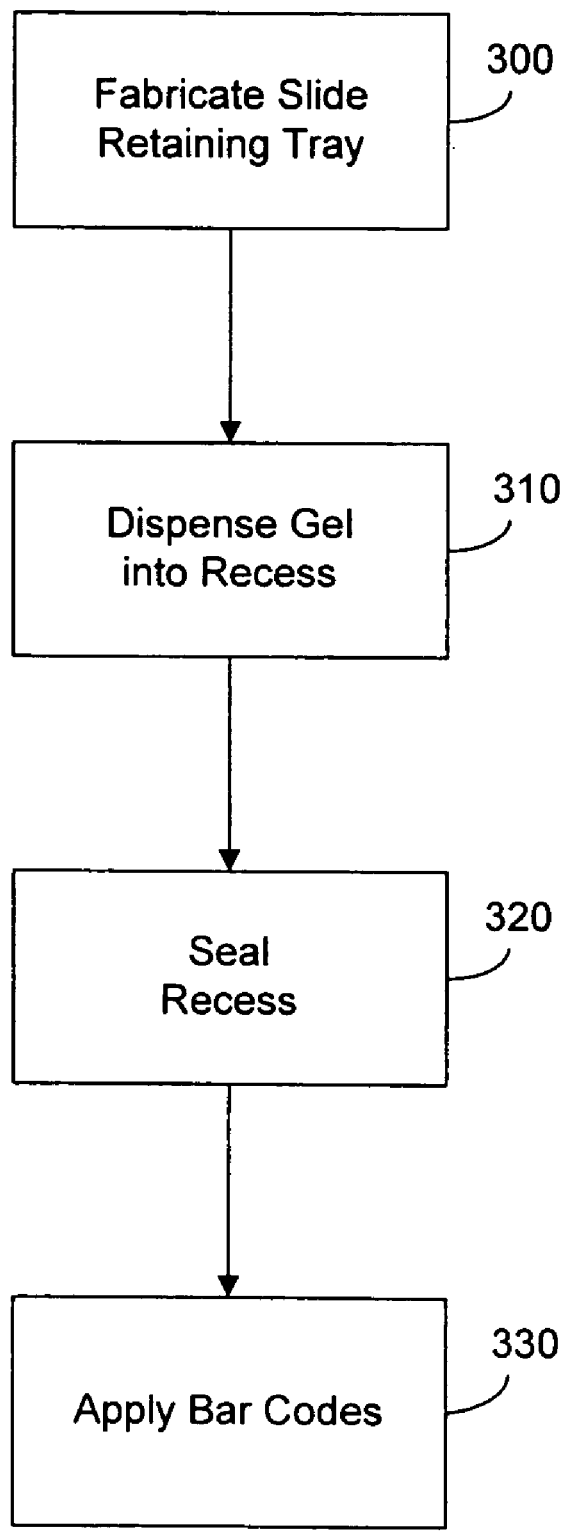
FIG. 3 is a flowchart depicting a method of manufacturing a slide retaining tray in accordance with the present invention.

A method of manufacturing a slide retaining tray 20 according to the principles of the present invention will now be described with respect to FIG. 3. As illustrated diagrammatically as box 300, the initial step involves fabricating the slide retaining tray 20. According to a preferred embodiment, slide tray 20 is fabricated from a polymeric material that is injection molded to form the desired structural shape. However, as would be understood to those of ordinary skill in the art, any fabrication process can be used or material selected that can achieve the desired structural features, without departing from the scope of the present invention.

Referring to box 310, the next step involves dispensing a desired quantity of gel into the gel retaining areas. For example, a predetermined amount of gel may inserted through apertures in the bottom surface of a recess, or alternatively can be inserted from above. After filling the recess, the optional apertures may be sealed by applying a tape or other covering. As illustrated diagrammatically as box 320, the next step involves sealing the recess. Any form of seal can be selected that can retain the gel in place and reduce vaporization and/or fluidic flow loss. For example, a mechanical seal can be applied as discussed above. Referring to box 330, the next step involves optionally applying identifiers to the slide retaining tray 20.

A method of using a slide retaining tray 10 in accordance with the principles of the present invention will now be described with respect to FIG. 4. As illustrated diagrammatically as box 420, the initial step involves selecting a slide retaining tray 20 based upon the type of gel or reagent(s) contained therein. Of course, the type of gel (i.e. reagent) contained within an individual tray 20 is dependent upon the type of test to be performed on a tissue sample. In other words, the initial step of selecting a slide retaining tray 20 may include the step of determining the type of test to be performed on the tissue sample. As illustrated diagrammatically as box 430, the next step involves optionally entering data concerning the reagent, tray etc. For example, optionally an identifier on the tray is read, such as for example swiping a bar code. Other ways of identifying the tray also might be used, such as machine identifiable tray features such as protrusion patterns or sizes, shapes etc. The tray identifier optionally identifies the reagent(s) contained in the tray. Alternatively, the identifying information can be inputted into a memory associated with the processing system such as via manual input via a keyboard or oral input such as via voice recognition software. In an optional embodiment, slide information can be input as well, such as via keyboard input, voice recognition input, machine identifier or shape. As discussed previously, the slide is positioned face down on the tray 10, and accordingly, an identifier preferably is not read when the slide is positioned on the tray or in a processing instrument. In an alternative, not preferred embodiment, the slide identifier can be read. As illustrated diagrammatically as box 450, the next step involves pulling the seal from the tray 20, thereby exposing the recess. Referring to box 460, the next step involves positioning the slide on the tray 20. Preferably, the slide is positioned such that the tissue sample is disposed between the slide and a platen. As illustrated diagrammatically as box 450, the next step involves optionally positioning the slide retaining tray 20 on a spring loaded heating/cooling pad 160.

As illustrated diagrammatically as box 470, the next step involves optionally positioning the slide retaining tray 20 on a spring loaded heating/cooling pad 160.

As illustrated diagrammatically as box 480, the next step involves liquefying a reagent matrix (i.e., the gel). This step may include the step of heating to form a melt. Alternatively, the matrix may be soluble in a solvent, which is added to the recess to dissolve it. Thus, the step of liquefying the matrix alternatively may include the step of dissolving the gel using a solvent. Referring to box 490, the next step involves flowing the liquefied reagent containing matrix over a drip surface into a gap between the platen and the slide. This step may be accomplished with the assistance of gravity by configuring the recess so that it is higher than the drip surface and the gap. For example, the slide tray may be configured, or mounted, so that the drip surface slopes downward from the reagent recess toward the gap. Referring to box 500, the next step optionally involves flushing the gap with wash fluids to prepare the tissue sample for subsequent tissue processing steps. As illustrated diagrammatically as box 501, the next step involves optionally dispensing additional reagents from the fluid dispensing apparatus 30 onto the drip surface. Referring to box 502, the next step involves drawing waste and excess fluid from the tray through a fluid return conduit into a waste reservoir.

Figure 4:
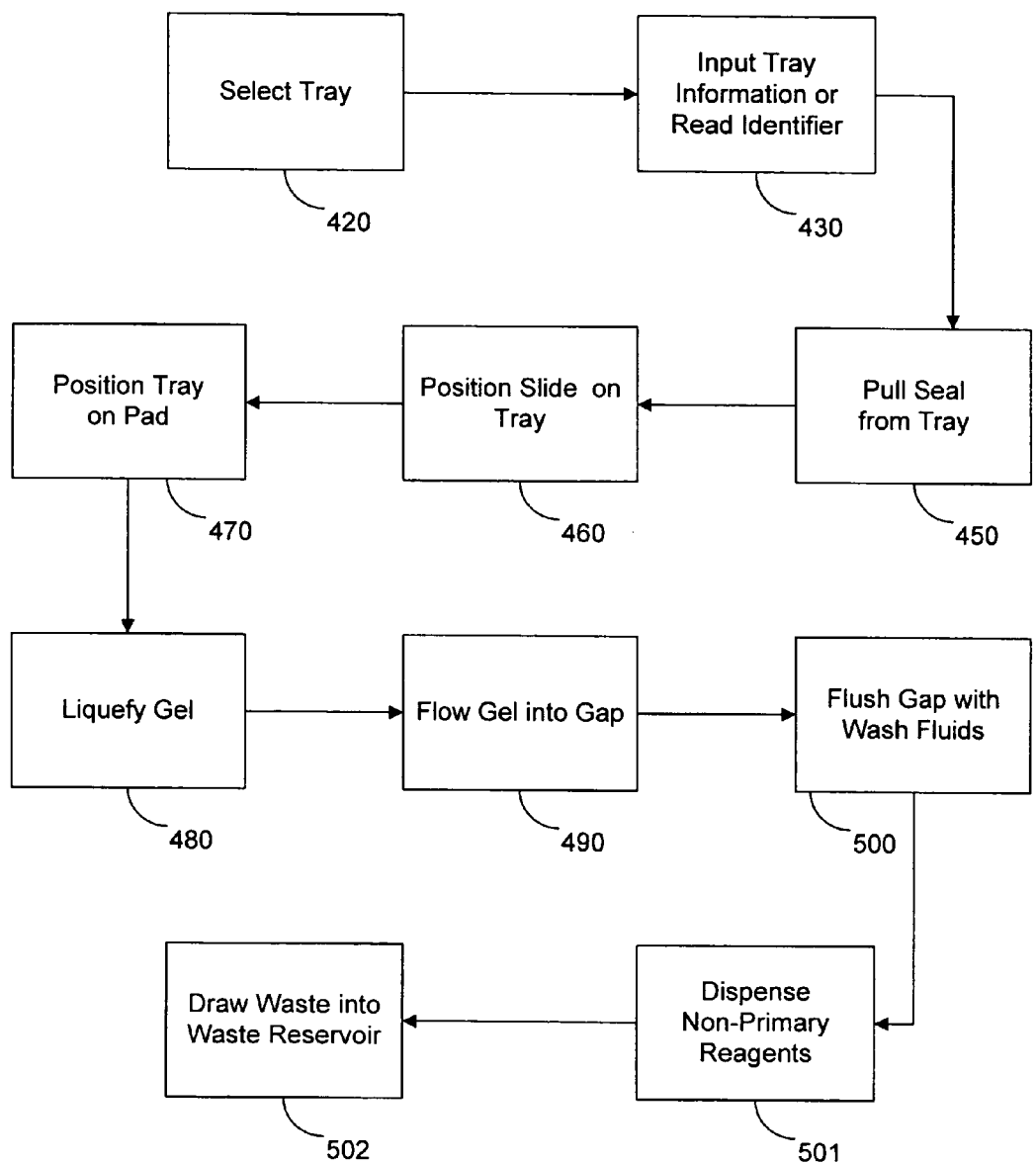
FIG. 4 is a flowchart depicting a method of using a slide retaining tray in accordance with the present invention.

With further reference to FIG. 4, the steps illustrated by boxes 430, 450, 460, and 470 may be performed in any order without departing from the scope of the present invention. Additionally, the step of inputting tray information 430 can optionally be performed after the step of positioning the slide on the tray (box 460), and either of these steps can be eliminated. Further, the step of pulling the seal from the tray 20 (box 430) can be performed at any time after the initial step of selecting a tray 20 based upon the type of gel contained therein (400).

Figure 5:
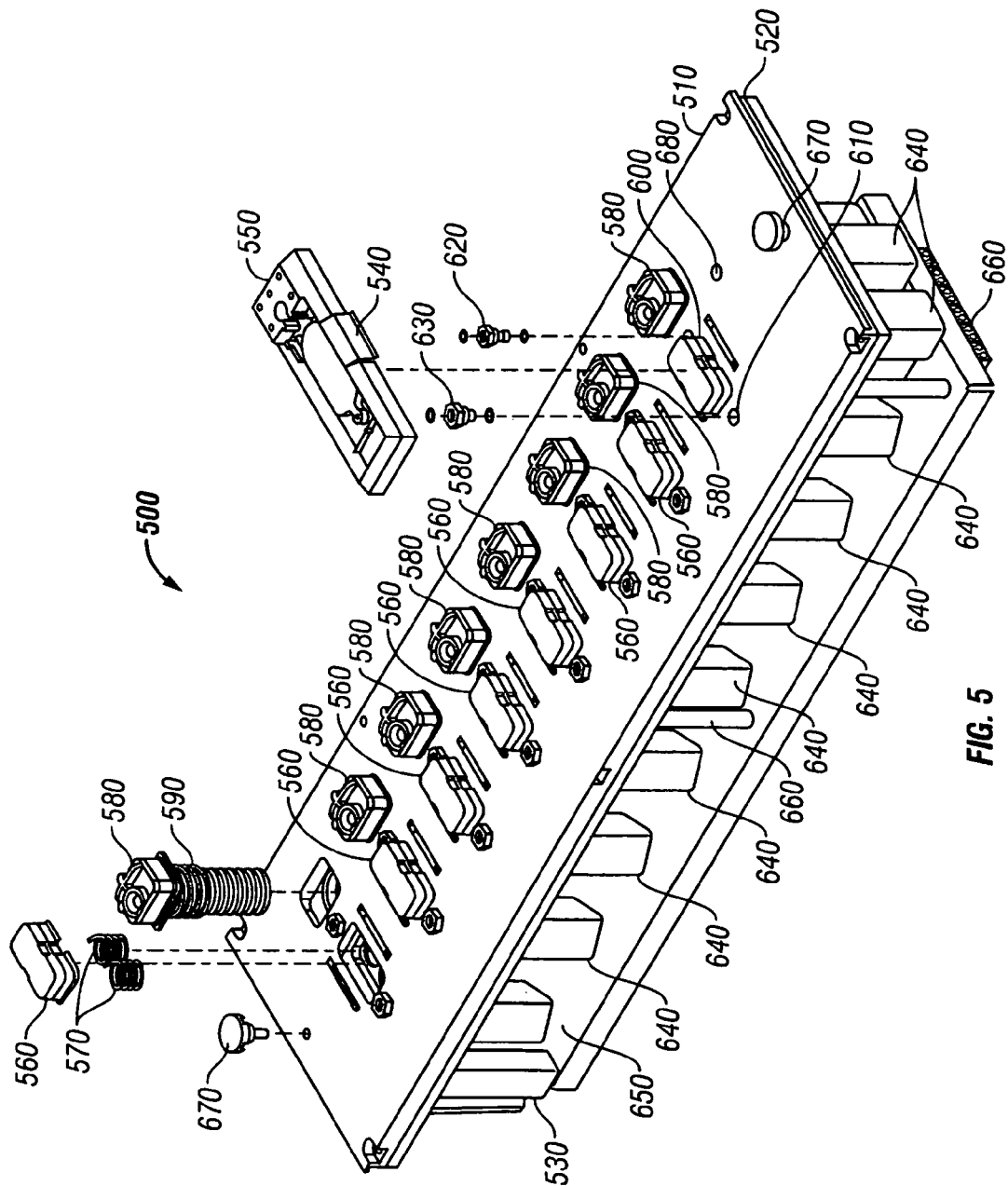
FIG. 5 is a partially exploded view of a manifold assembly in accordance with the present invention.

FIG. 5 illustrates a manifold assembly 500 according to an embodiment of the present invention. The manifold assembly 500 includes a platen 510 that forms a top portion of manifold assembly 500 and provides a mounting surface for the additional manifold assembly components. The platen 510 may include a plurality of tray mounting elements 530. The tray mounting elements 530 are features that allow a slide tray to be removably fixed to and located on platen 510. For example, mounting elements 530 may be slots configured to receive mounting tabs 540 located on each side of a slide retaining tray 550 (as shown). Alternatively, mounting elements 530 may be threaded or unthreaded holes that receive a removable fastener such as a screw or dowel rod extending through a slide tray or a post that is integrated into the slide tray. The tray mounting elements 530 may be substantially evenly spaced along a length of the platen 510 so that the trays 550 are mounted evenly spaced along the length of the platen 510. However, it shall be appreciated that the tray mounting features may have any orientation and need not be evenly spaced as would be appreciated by a person having ordinary skill in the art.

A manifold 520 is preferably provided immediately below the platen 510 and may be coupled thereto, for example by fasteners or processes such as welding. Manifold 520 is generally planar member that may be constructed from multiple plate components. Manifold 520 generally includes a network of fluid conduits that are configured for supplying reagents or other fluids to slide trays or for evacuating reagents or other fluids from slide trays. In an embodiment, fluid channels are etched directly into each of the manifold components and the components are stacked so that the fluid channels combine to form fluid conduits that extend through manifold 520. The manifold is preferably constructed from two plates of corrosion resistant, polymeric material. The plates may be joined by, for example, clamping, binding, welding or other known mechanically fastening technique.

According to an embodiment of the invention, the manifold 520 is formed from two (2) machined pieces of material. The material may be any material in which a channel may be mechanically etched, such as by machining, to result in a desired passageway and through which fluid may pass. Preferably, the material is a polymer and corrosion resistant, however, any such type of material may be used. The two (2) pieces of material preferably have matching machined passageways such that when the two (2) pieces are joined together, the passageways form one channel. The pieces may be joined by, for example, binding such as with an adhesive, clamping, welding, riveting, etc. One advantage of forming the manifold in such a manner is that precise tolerances for the channel may be achieved. Examples of suitable materials include acrylic, DELRIN (a registered trademark of E.I. du Pont de Nemours and Co. of Wilmington, Del.), ULTEM (a registered trademark of General Electric Co. of Pittsfield, Mass.), and stainless steel.

Heaters 560 may be provided to heat any desired portion of a tray 550 that is mounted on platen 510. Heaters 560 may include a heating pad constructed from a heat conductive material with an integrated heating element, as shown. The heating element may be molded into the heating pad or mounted to any surface of the heating pad. Heating pad may be constructed from any material known in the art such as polymers or metals and it may be manufactured by any process or combination of processes known in the art, such as molding and/or machining. Any type of heating element may be incorporated, such as a resistive heating wire or strip heater.

Heaters 560 may be spring-loaded by one or more springs 570 and configured to be inserted into apertures extending through platen 510 and/or manifold 520. Heaters 560 may also include retaining tabs that prevent heaters 560 from passing entirely through apertures when a tray 550 is not present. Springs 570 help to assure that heaters 560 are pressed into apposition with a bottom surface of tray 550 when it is mounted on platen and attached to mounting elements 530. Furthermore, the retaining tabs may be deflectable and the heaters 560 may be biased by springs 570 to facilitate removal of heaters 560 from the manifold assembly 500.

Heaters 560 may be positioned within manifold assembly 500 in any way desired. Preferably, the heaters 560 are substantially evenly spaced and located so that they underlie a central portion of trays 550 mounted on manifold assembly 500. It shall be appreciated that any number of heaters 560 may be provided to heat one or multiple locations on any tray 550. For example, a heater be provided adjacent to the reagent recess portion of a tray and a separate heater may be provided to heat a central portion of a tray 550.

Heaters 560 may be controlled independently or collectively. According to an embodiment of the present invention, heaters 560 are independently operated so that each tray 550 may be simultaneously heated to a different temperature. Alternatively, the heaters may be controlled collectively to heat all trays to a common temperature. As a further alternative, the heaters may be grouped so that a first group of heaters may be heated to a first temperature while a second group of heaters is heated to a second temperature and they may be grouped as desired.

One or more cooling assemblies may also be included in manifold assembly 500. In an embodiment, cooling is provided by thermoelectric cooler (TEC) assemblies 580. The TECs 580 may be used to cool portions of each tray 550 such as the reagent recess (described above) provided in the trays 550. Similar to heaters 560, the TECs 580 may be inserted into apertures that extend through manifold 520 and platen 510. TECs 580 may also be biased by a spring 590 to help assure contact between the TEC and tray 550 mounted on manifold assembly 500. One or more retaining tabs may be provided on TECs 580 so that the TEC may not pass entirely through the aperture when a tray 550 is not mounted on manifold assembly 550. The retaining tabs may be deformable to allow TECs to be removed from manifold assembly 500 and the bias of spring 590 facilitates removal of the TECs 580 from the manifold assembly 500. According to an embodiment of the present invention, the TECs 580 may be substantially evenly spaced such that the TECs 580 are provided adjacent a gel receiving portion, or reagent recess, of the trays 550 and substantially aligned with the trays 550. It shall be appreciated that TECs 580 may be replaced with alternative cooling mechanisms. For example, manifold assembly 500 may include conduits for transporting cooling fluids. The cooling conduits could be configured to transport the cooling fluid to any portion of the manifold assembly requiring cooling.

Fluid inlets 600 and outlets 610 are provided in platen 510 and manifold 520. Inlets 600 in the platen 510 are configured to mate with corresponding inlets 600 provided in the manifold 520 and inlet ports provided in trays 550. Likewise, outlets 610 in the platen 510 are configured to mate with outlets 610 provided in the manifold 520 and outlet ports provided in trays 550. Preferably, one inlet 600 and one outlet 610 are provided and located so that they correspond to inlet and outlet ports included at opposite ends of each tray 550. As shown in FIG. 5, such a configuration also corresponds to an inlet 600 and an outlet 610 positioned at opposite ends of each heater 560.

As mentioned above, inlets 600 and outlets 610 in the platen 510 and the manifold 520 are provided such that they are substantially aligned with apertures, or ports, provided in the slide receiving trays 550. By substantially aligning the inlets 600 and outlets 610 of the platen 510 and manifold 520 with the tray apertures complete fluid communication among the platen 510, manifold 520, and trays 550 is created. Inlet fittings 620 and outlet fittings 630 are provided with each inlet 600 and outlet 610, respectively. The inlet fittings 620 and the outlet fittings 630 provide a mechanism to create a more secure fluid link between the tray apertures with the inlets 600 and outlets 610 of the platen 510 and manifold 520. This increases the fluid communication among the platen 510, manifold 520, and the trays 550.

Valves 640 may be provided to control fluid flow through inlets 600 and outlets 610. The valves 640 are used to direct fluid flow (described in further detail below) through the manifold 520 to each of the inlets 600 and outlets 610. Depending on whether the valve 640 is provided at an inlet 600 or an outlet 610, the valve 640 may be a supply valve or a drain valve, respectively. The valves 640 are preferably mounted directly to manifold 520 at a top portion of the manifold assembly 500. According to an embodiment of the present invention, the valves 640 are three-way solenoid valves. However, any type of valve may be used including solenoid valves, ball valves or diaphragm valves and the valves may be configured in either normally closed or normally opened orientations as desired. Preferably, the valves are configured so that opening and closing of the valve is controlled electronically through a controller. It shall also be appreciated that the valves may be actuated in any way known in the art, such as for example electronically, pneumatically, hydraulically or combinations thereof.

A drip frame 650 may be included in manifold assembly 500 to prevent damage in the event a fluid leaks from manifold 520, valves 640 or tray 550. In particular, the drip frame 650 may be used to prevent the gel, reagent or other solutions or fluids from leaking onto a controller board 710 (described in further detail below). Drip frame 650 may be located below the valves 640 within manifold assembly 500. The drip frame 650 may be secured to the manifold 520 using, for example, a plurality of stand-offs 660 and mechanical fasteners. The stand-offs 660 may include mounting tips (described in further detail below with reference to FIG. 6) that are inserted into mounting apertures provided in the drip frame 650. Drip frame 650 may be constructed from any material known in the art such as polymers or metals. It is preferred that the drip tray material is resistant to corrosion from the reagents or other chemicals used in the tissue processing apparatus.

Inlets 600 are disposed at one end of the platen 510 and the outlets 610 preferably are at another end of the platen 510. By spatially separating the inlets 600 and outlets 610 on the platen 510, a pressure gradient can be introduced into a reaction chamber portion of tray 550 promoting fluid flow between the inlets 600 and outlets 610. In an illustrated embodiment, inlets 600 are situated at the ends of heaters 560 that are adjacent the TECs 580 and the outlets 610 are at the opposite ends of heaters 560. By positioning the inlets 600 adjacent the TECs 680, all of the fluids introduced into the reaction chamber can be introduced from the same end promoting fluid flow in a single direction and simplifying the layout of fluid conduits through manifold 520. Moreover, fluid flow can be further promoted in a direction by providing an incline on platen 510 thereby slightly angling the tray 550 when positioned on the platen 510 promoting capillarity (i.e., capillary action) induced flow as directed by the slide angle relative to the platen.

Optional fasteners 670 may be provided at opposite ends of the platen 510. The fasteners 670 may be provided to facilitate installation and removal of a manifold assembly 500 from a tissue processing system. Fasteners 670 may be thumbscrews, winged screws or any other fastener that may be easily manipulated by hand. Alternatively, fasteners 670 may be configured to require additional tools and/or a technician to install or remove the manifold assembly. In further embodiments, the manifold assembly may be maintained within a reagent dispensing system with electronically controlled locking mechanisms. Handles or other gripping features may be provided so that the manifold assembly may be easily gripped and removed from the system.

A priming fitting 680 may also be provided in platen 510 and manifold 520. Priming fitting 680 may be used to prepare, or prime, cartridges 50 to provide fluid to trays 550. Cartridges 50 are prepared by pumping a fluid dispensing assembly that is included in cartridge 50 so that any air or other contaminants within the fluid dispensing assembly is expelled. Clearing air and contaminants from the dispensing assembly assures that a selected volume of uncontaminated fluid is delivered from cartridge 50 during processing. During the priming process of cartridge 50 fluid is expelled from the dispensing assembly into priming fitting 680. Preferably, priming fitting 680 is generally aligned with the locations of the drip surfaces included on trays 550 on an outlet end of manifold 520. Similar to inlets 600 and outlets 610, priming fitting 680 may be provided with a priming valve so that the opening and closing of a fluid conduit extending from priming fitting 680 into the fluid network of manifold 520 may be controlled.

Figure 6:
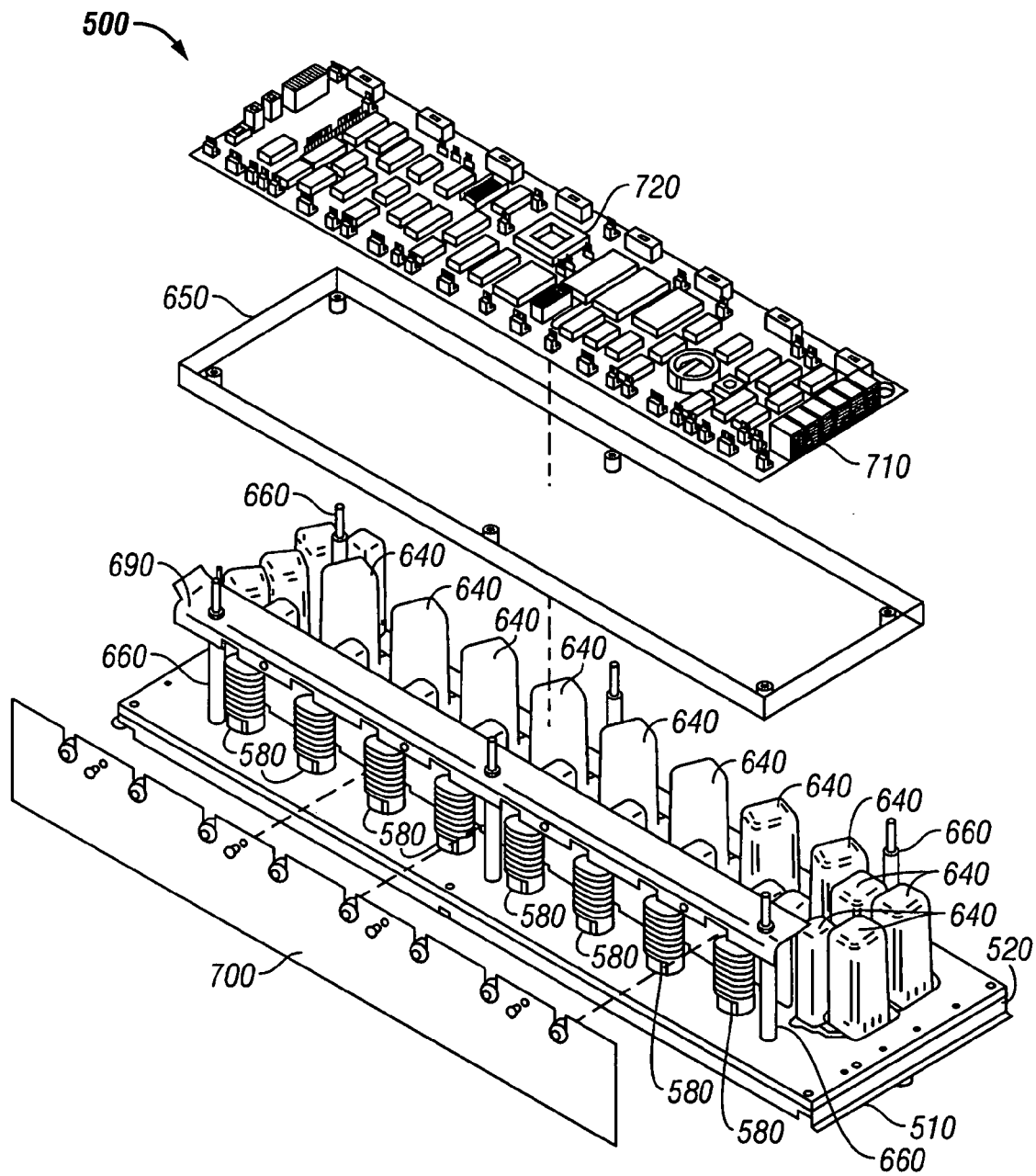
FIG. 6 is an exploded view of a manifold assembly in accordance with the present invention.

FIG. 6 illustrates an exploded view of manifold assembly 500 according to an embodiment of the present invention. The manifold assembly 500 is shown in an upside-down orientation. The TECs 580, valves 640, and stand-offs 660 are mounted to the manifold 520 and manifold platen 510. As shown in FIG. 6, the TECs 580 are provided on one side and evenly spaced along a length of the manifold 520. The valves 640 are provided on a side of manifold 520 opposite the TECs 580 and positioned such that each valve 640 is substantially aligned with an inlet 600 or outlet 610.

Manifold 520 may include fluid connection ports that are configured to mate with corresponding fluid connection ports in the system so that the supply and drain paths of the manifold assembly are able to fluidly communicate with the supply and drain conduits of the system. Any connection port may be employed. For example, tubing may be extend between ports on both the manifold assembly and the system. Alternatively, fluid connectors may be utilized that allow for easy integration and removal of each manifold assembly from the system. Such fluid connectors allow for easy maintenance. Compressible members, such as o-rings, may be provided to seal fluid connections between manifold 520 and connection ports of the system.

A support member 690 may be mounted on a plurality of stand-offs 660. The support member 690 may be used to support a panel 700 and may also be used to support drip frame 650 such that the drip frame 650 is spaced at a predetermined distance from the TECs 580 and valves 640. Support member 690 may be constructed as a single component mounted to a plurality of stand-offs 660 (as shown) or it may include multiple individual mounting tabs each mounted to an individual stand-off 660. Support member 690 may include threaded holes for mounting a panel 700 within manifold assembly 500. A divider portion may also be included in support member 690 that provides a wall located generally between TECs 580 and valves 640 so that support member 690 in conjunction with panel 700 create a cooling air channel. Support member 690 may be constructed from any material known in the art such as a polymer or metal and it may be formed by molding, machining and/or thermal or hydro forming sheet material.

The panel 700 may be used to create an air channel to allow cooling air to flow between and amid the TECs 580. The panel 700 may be, for example, a strip of sheet metal or other material that creates a cooling air chamber in conjunction with support member 690. The panel 700 may be attached to the support member using any known fastening mechanisms such as, for example, screws, rivets, bolts, clamps, welding, soldering or other fastener.

A peripheral controller board 710 may be provided in manifold assembly 500. As shown in FIG. 6, controller board 710 may be mounted on a side of the drip frame 650 opposite the TECs 580 and valves 640. Preferably, the drip frame 650 surrounds the controller board 710 such that the drip frame 650 reduces a likelihood of reagents or other fluids leaking in the manifold assembly from flowing onto the controller board 710.

The controller board 710 may include one or more controllers that may be used to control fluid flow through the manifold 520, operation of heaters 560, operation of TECs 580 and/or cooling of the components within manifold assembly 500. In particular, the flow of fluid through manifold 520 may be controlled by controlling each of the valves 640 included in manifold assembly 500. The controller board 710 may also control operation of the heaters 560 and TECs 580 individually or in groups.

Figure 7:
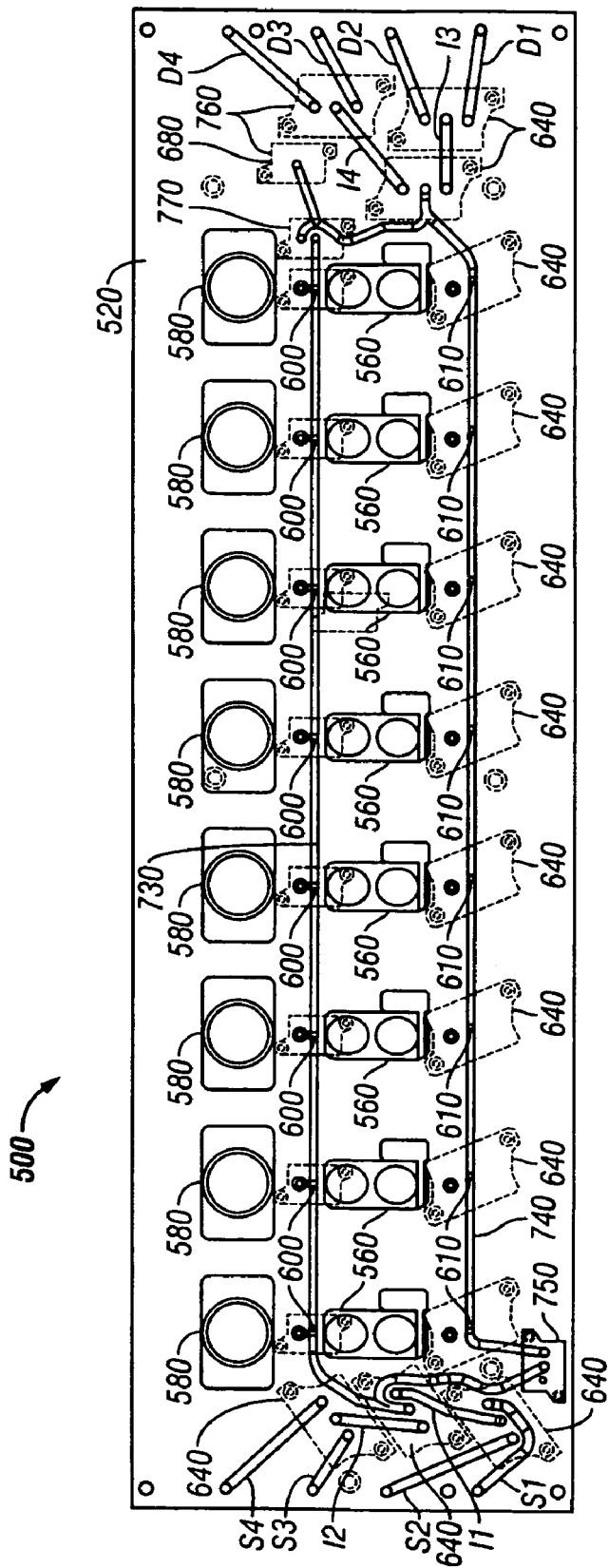
FIG. 7 is a top view of an embodiment of a manifold assembly showing fluid paths in accordance with the present invention.

The controller board 710 preferably includes a central processing unit (CPU) 720 that processes tissue staining procedures. The staining procedures identifies, among other information, tissues to be stained, reagents to be used, tissue tray locations, amount of time to expose a tissue sample to a reagent, and washing cycle. The CPU 720 may be used to control the valves 640 such that direct fluid paths are provided from a reagent supply container to a desired tray 550 or from a particular tray 550 to a waste container FIG. 7 illustrates a configuration of fluid conduits through manifold 520 of manifold assembly 500 according to an embodiment of the present invention. As described above, the manifold assembly 500 is provided with a plurality of heaters 560, TECs 580, and valves 640 that control fluid flow through fluid conduits in manifold 520. In the present embodiment, a fluid supply line 730 is provided along a length of the manifold 520 adjacent the inlets 600. The supply line 730 is in fluid communication with the plurality of valves 640 that are adjacent to and in fluid communication with the inlets 600, referred to as supply valves. A plurality of supply paths S1-S4 are provided that are in fluid communication with the supply line 730 upstream from the supply valves. The supply paths S1-S4 provide a fluid path between supply containers and supply line 730 and allow the system to direct reagent or other solution or fluid from a supply container (shown in FIG. 9) to inlets 600 through supply line 730. In the present embodiment, each of supply paths S1-S4 is fluidly coupled to supply line 730 through a plurality of valves 640. As shown, supply paths S1 and S2 are coupled to an intermediate supply line I1 through a first valve 640, supply paths S3 and S4 are coupled to a second intermediate supply conduit I2 through a second valve 640, and intermediate supply conduits I1 and I2 are coupled to supply line 730 through a third valve 640. Although only four (4) supply conduits are shown, any number of supply conduits and valves may be used to provide fluid from any number of supply containers to the supply line 730. Furthermore, it shall be appreciated that one or more supply conduits may extend directly to the supply valves or the supply conduits may be grouped into a plurality of supply lines rather than being fluidly coupled to a single common supply line 730.

In operation, the supply paths S1-S4 receive reagent or other types of solutions or fluids from a supply source (not shown). The supply paths S1-S4 are in fluid communication with the supply line 730 via supply valves 640, as described above. The supply valves 640, controlled by a controller, direct fluid from the supply paths S1-S4 to the supply line 730 and to a particular slide receiving tray (not shown). By controlling each of the valves 640, this enables the distribution of fluids to or from individual trays. For example, a staining procedure may require that a specific reagent be applied to a tissue sample provided on the tray. This reagent may be stored in a supply container that is only in fluid communication with supply path S3. The controller may be used to close the supply valves 640 in communication with the supply paths S1-S2 and S4 and to open the supply valve 640 in communication with supply conduit S3. In addition, the controller may be used to open valve 640 that couples intermediate conduit I2 and supply line 730. This prevents fluid from supply paths S1-S2 and S4 from entering either the intermediate supply conduits or the supply line 730 and only permits fluid from the supply conduit S3 to enter intermediate supply conduit I2 and supply line 730.

Next, supply valve 640 that is in communication with the inlet 600 for the desired tray is also placed in the opened position. In addition, supply valves 640 not in communication with the inlet for the desired tray are placed in a closed position. By opening only those supply valves 640 that are in a fluid path between a predetermined supply source and a desired slide receiving tray, a direct path is created from that particular supply source to an inlet of the desired tray. Various mechanisms may be used to urge the reagent or other fluid through supply paths S1-S4 and supply line 730 using, for example, a pressure source applied to the supply source (described in further detail below).

A drain line 740 may also be provided along a length of the manifold 520 adjacent the outlets 610. The drain line 740 is in fluid communication with each of the valves 640 that are adjacent to and in fluid communication with the outlets 610, referred to as drain valves. A plurality of drain paths D1-D4 are provided that are in fluid communication with the drain line 740. The drain paths D1-D4 direct reagent or other solution or fluid from the drain line 740 to, for example, a waste container (shown in FIGS. 9A and 9B). Similar to the supply conduits described above, drain paths D1-D4 are in fluid communication with drain line 740 through a plurality of valves 640 and intermediate drain conduits. In particular, drain paths D1 and D2 are in fluid communication with a first intermediate drain conduit I3 through a first valve 640, drain paths D3 and D4 are in fluid communication with a second intermediate drain conduit I4 through a second valve 640, and intermediate drain conduits I3 and I4 are in fluid communication with drain line 740 through a third valve 640. Although only four (4) drain paths are shown, any number of drain paths and valves may be used to provide fluid flow from the drain line 740 to a desired number of waste containers or other outlet.

Drain paths D1-D4 are in fluid communication with outlets 610 via the drain valves, drain line 740 and the intermediate drain conduits. According to an embodiment of the present invention, the drain line 740 may also be in fluid communication with the supply line 730 via an outlet purge valve 750. The drain line 740 is used to drain reagents or other solutions or fluids from a slide receiving tray that were introduced onto the tray through the supply line 730. Various methods may be used to urge fluid into the drain conduits. For example, a vacuum pump may be applied to a waste container to draw fluids from drain line 740 and/or one or more slide trays.

The controller may control the positions of any of the valves included in the manifold assembly 500. As discussed above, the controller generally operates the valves 640 based on one or more staining procedures being processed by the CPU. The CPU determines which valves 640 are necessary to have in opened and closed positions throughout the procedure such that the desired fluid paths are created at each step from a supply source to a desired slide receiving tray or from a particular slide receiving tray to a waste container. This determination may be based on instructions provided to the controller for the particular staining procedure.

It should be noted that any combination of opened and closed valve positions may be used to create any desired fluid path. For example, all supply valves 640 in communication with the supply paths S1-S4 and one or more of the supply valves 640 in communication with the inlets 600 of the slide receiving trays may be in an opened position. Alternatively, a portion the supply valves 640 in communication with the supply paths S1-S4 and one or more of the supply valves 640 in communication with the inlets 600 of the slide receiving trays may be in an open position. One of ordinary skill in the art will realize that the valves 640 may be in any combination of opened and closed positions to result in any desired fluid path.

Figure 8:
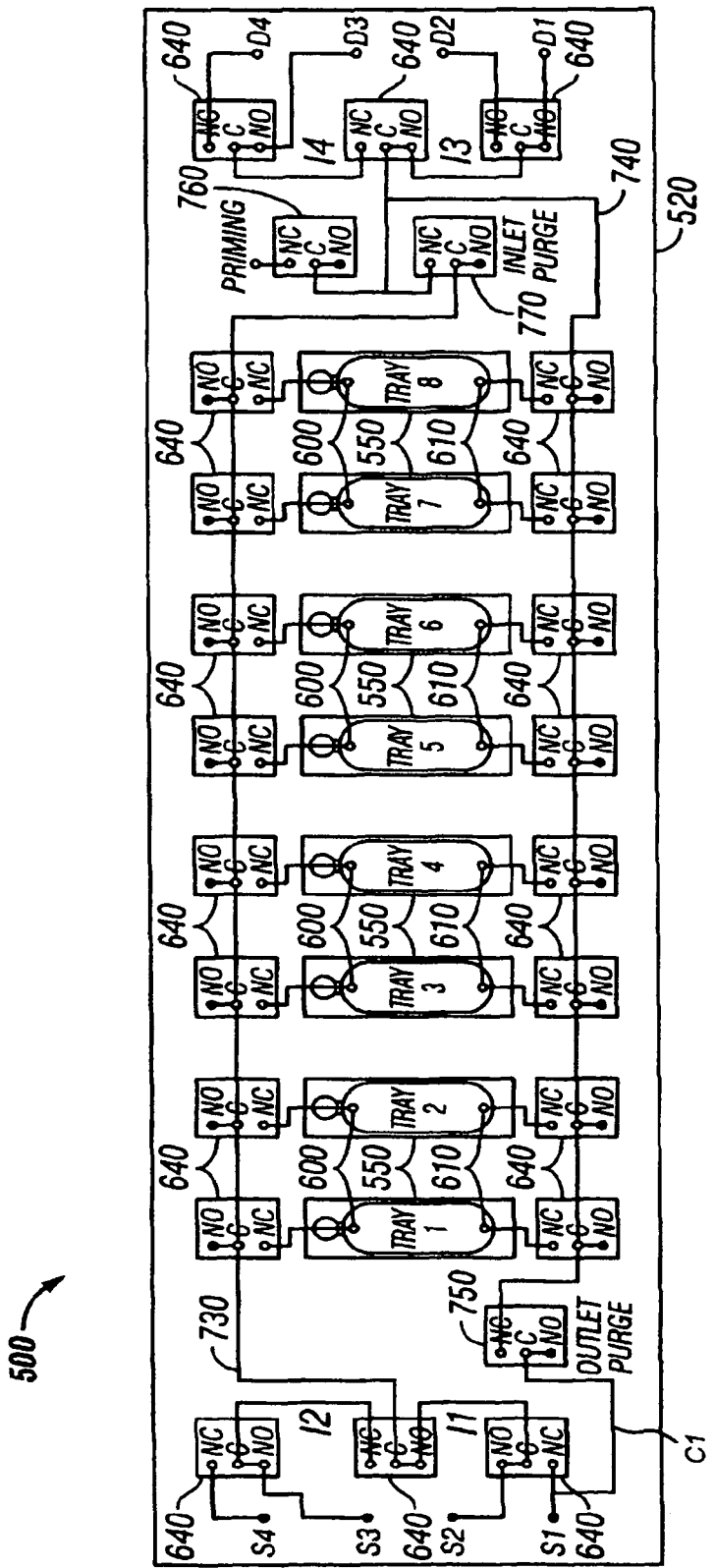
FIG. 8 is a schematic diagram of the fluid paths and valves of an exemplary manifold assembly in accordance with the present invention.

FIG. 8 is a fluid schematic diagram of a manifold 520 of a manifold assembly 500 according to an embodiment of the present invention. The diagram schematically illustrates a plurality of trays 550, valves 640, supply paths S1-S4, and drain paths D1-D4, intermediate conduits I1-I4, a cleaning path C1, a supply line 730, and a drain line 740. Each of the supply paths S1-S4 and drain paths D1-D4 are coupled in fluid communication with the supply line 730 and drain line 740, respectively, through a plurality of valves 640. Each tray 550 has an inlet 600 and an outlet 610. The inlets 600 are in fluid communication with a corresponding supply valve 640 and the outlets 610 are in fluid communication with a corresponding drain valve 640.

In addition to the supply and drain valves, a priming valve 760, an inlet purge valve 770, and an outlet purge valve 750 are also provided. The priming valve 760 may be used to dispose of fluid expelled from a cartridge 50 during a priming process in preparation for dispensing any type of reagent or other fluids such as, for example, distilled water, buffering solutions, dewaxing solutions, and/or washes to a slide receiving tray 550. In the present embodiment, priming valve 760 is fluidly coupled to an outlet end of supply line 730. The inlet purge valve 770 is also fluidly coupled to supply line 730 at an outlet end and may be used to purge the inlets 600 and supply line 730 of undesired remaining fluid. For example, distilled water from a supply source may be injected into supply line while all of inlets 600 are in a closed position so that the distilled water may flush any remaining reagents or other unwanted fluids. Cleaning path C1 provides fluid communication between supply path S1 and outlet purge valve 750 so that the outlets of trays 550 may be purged. The outlet purge valve 640 may be used to purge the outlets 610 and drain line 740 of undesired materials. The valves 640, controlled by a controller, operate to provide desired fluid paths either from a supply source or to a waste container as described above. That is, the controller positions each of the valves 640 in an opened or closed position, based on a staining procedure being processed by the CPU of the controller, to result in a desired fluid path either from a supply source or to the waste container.

It shall be appreciated that the valves may be oriented to provide any default fluid configuration desired. In particular, each conduit coupled to a particular valve may be coupled to a "normally opened" or a "normally closed" connection port to provide a desired default fluid path. For example, in the embodiment shown in FIG. 8, supply path S1 is coupled to the normally closed connection port of a first valve 640 and supply path S2 is coupled to a normally opened connection port of the same valve. As a result, by default, fluid flowing through supply path S2 will be free to flow through that valve unless the valve is configured by the controller to open the normally closed connection port, thereby allowing fluid from supply path S1 to flow through the valve. Similarly, the inlets 600 and outlets 610 of the trays are each connected to a normally closed connection port of a respective valve. Therefore, by default, fluid is prevented from flowing into or out of each tray unless the controller specifically configures the respective valve so that the inlet 600 or outlet 610 is in an opened position.

Figure 9A:
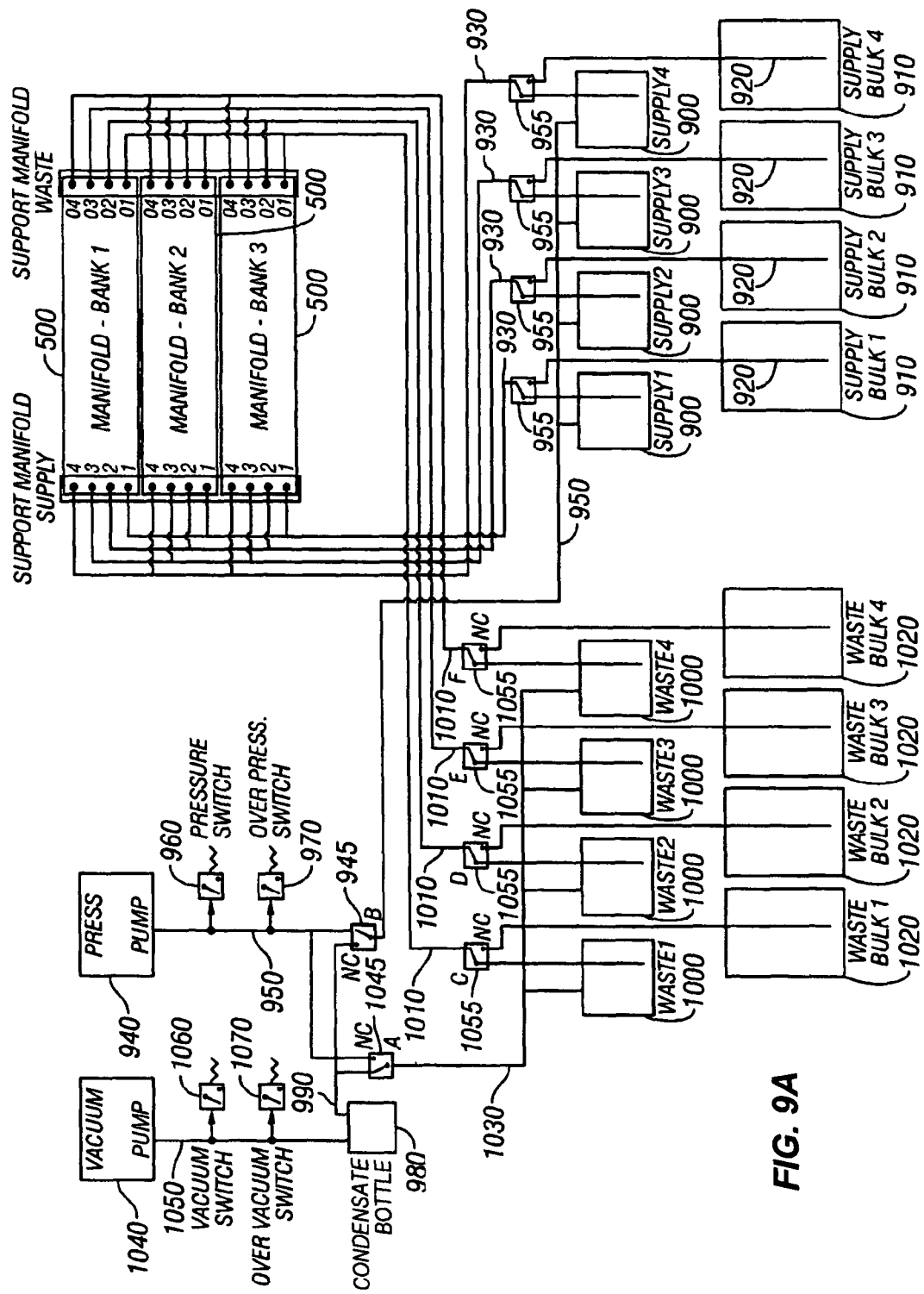
FIGS. 9A and 9B are plumbing schematic diagrams of alternative embodiments of a tissue processing system in accordance with the present invention.
Figure 9B:
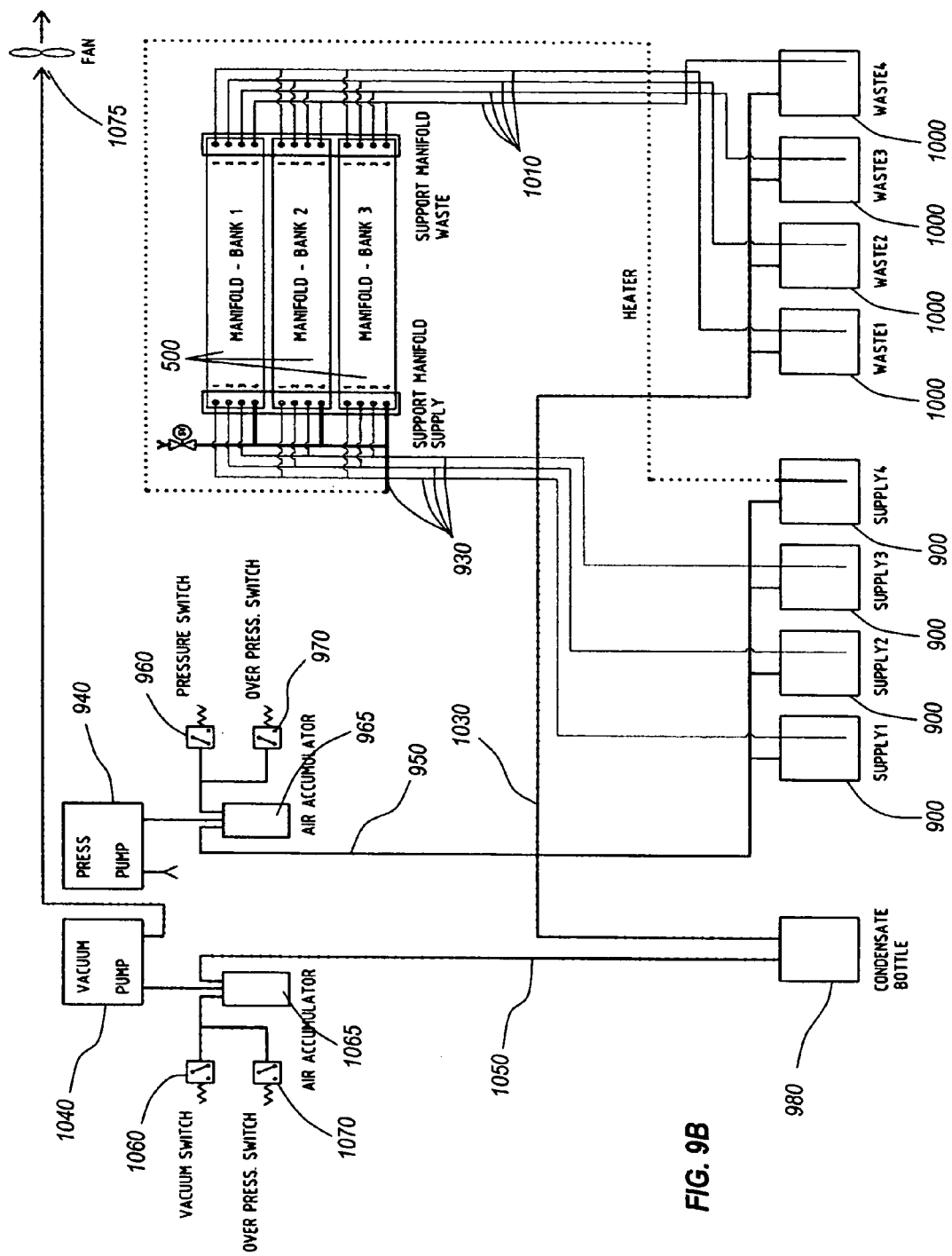

FIGS. 9A and 9B are plumbing schematic diagrams of a tissue processing system according to embodiments of the present invention. As shown in FIG. 9A, the tissue processing system is provided with three (3) manifold assemblies 500. Each manifold assembly 500 includes a manifold 520 that is provided with four (4) supply paths S1-S4 provided on one end and four (4) drain paths D1-D4 provided on an opposite end. The supply paths S1-S4 are in fluid communication with supply bottles 900 via supply valves 955 and supply conduits 930. The supply valves 955 are configured so that bottles 900 may be placed in fluid communication with either supply conduits 930 or bulk supply containers 910. The supply valves 955 also enable reagent or other solutions or fluids to travel from the bulk supply containers 910 to the supply bottles 900 via a bulk supply line 920 and from the supply bottles 900 to the supply paths S1-S4 via supply conduits 930.

The supply bottles 900 may also be placed in communication with a pressure pump 940 via a vacuum pressure select valve 945 and a pressure line 950. The pressure pump is configured to pressurize the contents of supply bottles 900 to drive the contents through the fluid network of the system. The pressure pump 940 may have a pressure switch 960 that enables pressure pump 940 to be maintained at a predetermined level and an over-pressure switch 970 that automatically turns off the pressure pump 940 when the pressure created by pressure pump 940 exceeds a predetermined amount.

As mentioned above, pressure pump 940 is used to create a pressure within the supply bottles 900 that urges fluid stored in the supply bottles 900 to travel through the valves 955 and supply conduits 930 into one or more of the manifold assemblies 500 via the supply paths S1-S4. The vacuum pump in conjunction with valves 955, 945 being positioned to allow fluid communication between supply bottles 900 and bulk supply containers 910 may be used to draw fluid from the bulk supply containers 910 into the supply bottles 900 to fill the supply bottles 900. A set of vacuum pressure select valves 945, 1045 is used to switch the line between pressure and vacuum to draw liquid from the bulk container into the supply bottles and to empty the waste bottles into the bulk container.

A condensate bottle 980 is also included in the system. The condensate bottle 980 may be used to collect excess fluid to prevent it from getting into the vacuum pump. Also, if a supply bottle 900 has a one (1) liter capacity and the vacuum pump 1040 causes 1.2 liters of fluid to be dispensed into the supply bottle 900, the excess 0.2 liters of fluid may travel through the vacuum pressure select valve 945 and an overflow line 990 into the condensate bottle 980. Preferably, bottle level sensors are used to shut-off the vacuum pump 1040 before a large amount of excess fluid is dispensed into a supply bottle 900.

The manifold assemblies 500 are also in fluid communication with waste bottles 1000 via waste paths D1-D4, waste conduits 1010, and drain valves 1055. The waste bottles 1000 may also be placed in fluid communication with bulk waste containers 1020 via drain valves 1055 through bulk waste lines 1060. Vacuum pump 1040 is provided and is configured to apply a vacuum to the waste bottles 1000 over a vacuum line 1050 and through vacuum pressure select valve 1045. The vacuum pump 1040 may be used to create a vacuum within the waste bottles 1000 that urges fluid provided on or in the slide receiving trays provided on the manifold assemblies 500 to travel through the drain paths D1-D4, drain conduits 1010 and drain valves 1055 into one or more of the waste bottles 1000.

The vacuum pump 1040 may also be used to draw fluid from bulk supply containers 910 into supply bottles 900 by placing vacuum pump 1040 into fluid communication with supply bottles 900 through vacuum pressure select valve 945. In addition, waste material in waste bottles 1000 may be transferred into bulk waste containers by placing waste bottles in fluid communication with pressure pump 940 via vacuum pressure select valve 1045 and by placing a desired waste bottle in fluid communication with a desired bulk waste container 1020 via a drain valve 1055.

The vacuum pump 1040 preferably includes a vacuum switch 1060 that enables vacuum pump 1040 to maintain a predetermined vacuum level in the bottles and an over-vacuum switch 1070 that automatically turns off the vacuum pump 1040 when the vacuum created exceeds a predetermined amount. According to an embodiment of the present invention, the bulk supply containers and the bulk waste containers are housed external to the reagent dispensing system.

The waste bottles 1000 may be designated as either a hazardous waste bottle or a non-hazardous waste bottle. Therefore, when draining fluid from a slide receiving tray, the controller (described above) determines whether the fluid in the tray is hazardous or non-hazardous. Upon making this determination, the controller positions each of the valves 640 in the respective manifold assembly 500 either an opened or a closed position such that a direct fluid path is created from the tray through the appropriate drain path D1-D4 and to a predetermined waste bottle 1000 that is designated for that particular type of waste.

Referring to FIG. 9B, another embodiment of the plumbing schematic will be described. Similar to the embodiment described above, the tissue processing system schematically illustrated in FIG. 9B includes three (3) manifold assemblies 500, each of which is provided with a manifold that has four (4) supply paths located on one end and four (4) drain paths located on the opposite end. Additionally each supply path is in fluid communication with a supply bottle 900 via a supply conduit 930 and each drain path is in fluid communication with a waste bottle 1000 via a drain conduit 1010.

The embodiment of FIG. 9B also includes a pressure pump 940 and a vacuum pump 1040, however pressure pump 940 is dedicated to supply bottles 900 through pressure line 950 (i.e., pressure pump 940 is in fluid communication with supply bottles 900 but not waste bottles 1000 as in the previous embodiment) and vacuum pump 1040 is dedicated to waste bottles 1000 through vacuum lines 1050, 1030. In the present embodiment, the system has been simplified by omitting bulk waste and bulk supply bottles.

Pressure pump 940 may have a pressure switch 960 that enables pressure pump 940 to be maintained at a predetermined level. In addition, an over-pressure switch 970 may be coupled to pressure pump 940 that automatically turns off pressure pump 940 when the pressure created by pressure pump 940 exceeds a predetermined amount.

Vacuum pump 1040 preferably includes a vacuum switch 1060 that enables vacuum pump 1040 to maintain a predetermined vacuum level in the bottles and an over-vacuum switch 1070 that automatically turns off vacuum pump 1040 when the vacuum created exceeds a predetermined amount. Furthermore vacuum pump 1040 may be in fluid communication with a fan 1075 so that gas pumped from the system may be expelled. A condensate bottle 980 is also included in the system between vacuum line 1050 and vacuum line 1030. The condensate bottle 980 may be used to collect excess fluid to prevent it from getting into the vacuum pump. In addition, air accumulators 965, 1065 may be included with each of pressure pump 945 and vacuum pump 1040. It shall be appreciated that the system preferably includes supply and waste valves (not shown) that may be used to control fluid flow from supply bottles 900 or into waste bottles 1000. It shall be further appreciated that any of the fluid lines included in the system may be heated or cooled as desired.

Figure 10:
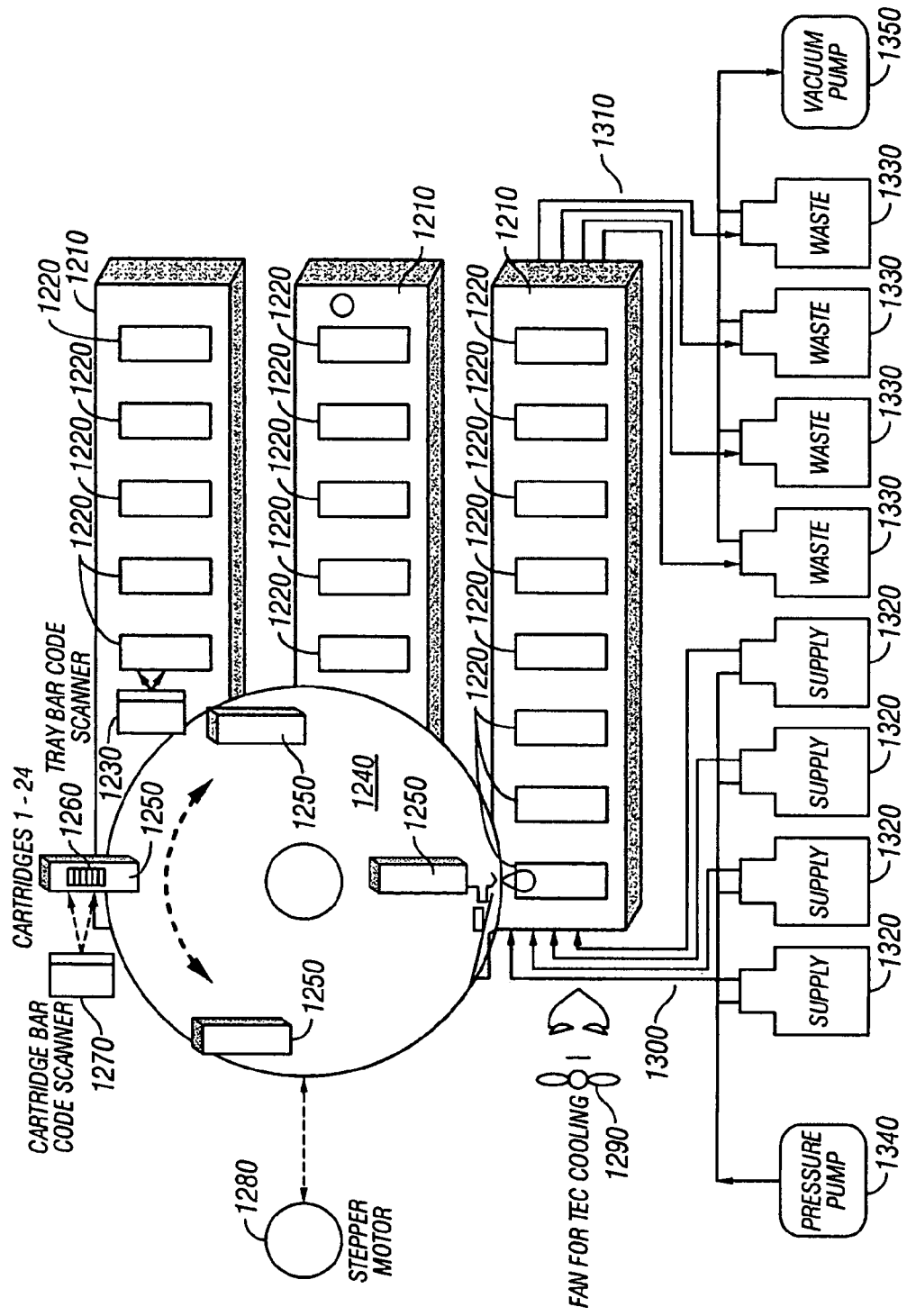
FIG. 10 is a schematic diagram of a tissue processing system in accordance with the present invention.

FIG. 10 illustrates a tissue processing system 1200 according to an embodiment of the present invention. The tissue processing system 1200 includes three (3) manifold assemblies 1210 on which eight (8) slide receiving trays 1220 are supported. Preferably, each of the trays 1220 has a bar code or other identifier (not shown) associated therewith. A tray bar code scanner 1230 may be provided to scan the bar codes associated with the trays 1220 and obtain information regarding a sample provided on the tray. The information may include, for example, patient information, tissue type, reagent information, etc. Preferably, one bar code scanner is provided for each manifold assembly 1210 that is movable with respect to the trays.

The tissue processing system 1200 also includes a carousel 1240. The carousel 1240 holds a plurality of reagent cartridges 1250. Preferably, each reagent cartridge 1250 has a bar code 1260 or other identifier that is read by a cartridge bar code scanner 1270. The carousel 1240 may rotate in a clockwise or counter-clockwise direction and the cartridge bar code scanner 1270 may be mounted stationary with respect to the carousel so that bar code scanner 1270 may scan each reagent cartridge bar code 1260.

The carousel 1240 may also be provided with three (3) tray bar code scanners 1230. The tray bar code scanners 1230 are preferably positioned such that when the carousel 1240 is moved over a length of the manifold assemblies 1210, the tray bar code scanners 1230 scan the bar codes associates with each of the trays 1220.

Carousel 1240 is preferably actuated so that it is capable of both translating and rotating in tissue processing system 1200. An electric motor 1280, such as a stepper motor or a constant reluctance motor, may be used to translate the carousel 1240 over the length of the manifolds 1210. It shall be appreciated that any mechanism that converts the rotary motion of the motor to linear motion may be utilized. For example, carousel 1240 may be mounted on a movable cart and a belt or chain drive may couple the movable cart to motor 1280. Alternatively, a lead or ball screw mechanism may be used to movably couple carousel 1240 to motor 1280. It shall be appreciated that hydraulic and/or pneumatic actuators may be used in addition to or as an alternative to the actuator described above.

Although only one is shown, each manifold assembly 1210 may also include a fan 1290 that may be used to cool the TECs of the manifold assembly 1210. Similarly, each manifold assembly 1210 may also have one or more supply conduits 1300 and one or more drain conduits 1310. Similar to the systems described above, supply conduits 1300 are in fluid communication with supply bottles 1320 and the drain conduits 1310 are in fluid communication with the waste bottles 1330.

A pressure pump 1340 may be included and configured to pressurize the contents of supply bottles 1320 so that the reagent or other fluid provided in the supply bottles 1320 is urged to enter the supply conduits 1300 and manifold assembly 1210. The contents of the supply bottles are preferably provided to an individually selectable tray 1220 using a controller, valves, supply paths, and supply lines as described above.

A vacuum pump 1350 may also be included and configured to apply vacuum pressure to the waste bottles 1330 causing the reagent or other fluid in the trays 1220 to drain from the trays 1220 through the drain conduits 1310. The reagent other fluid is preferably removed from an individually selectable tray 1220 using a controller, valves, drain paths, and drain lines as described above.

Figure 11:
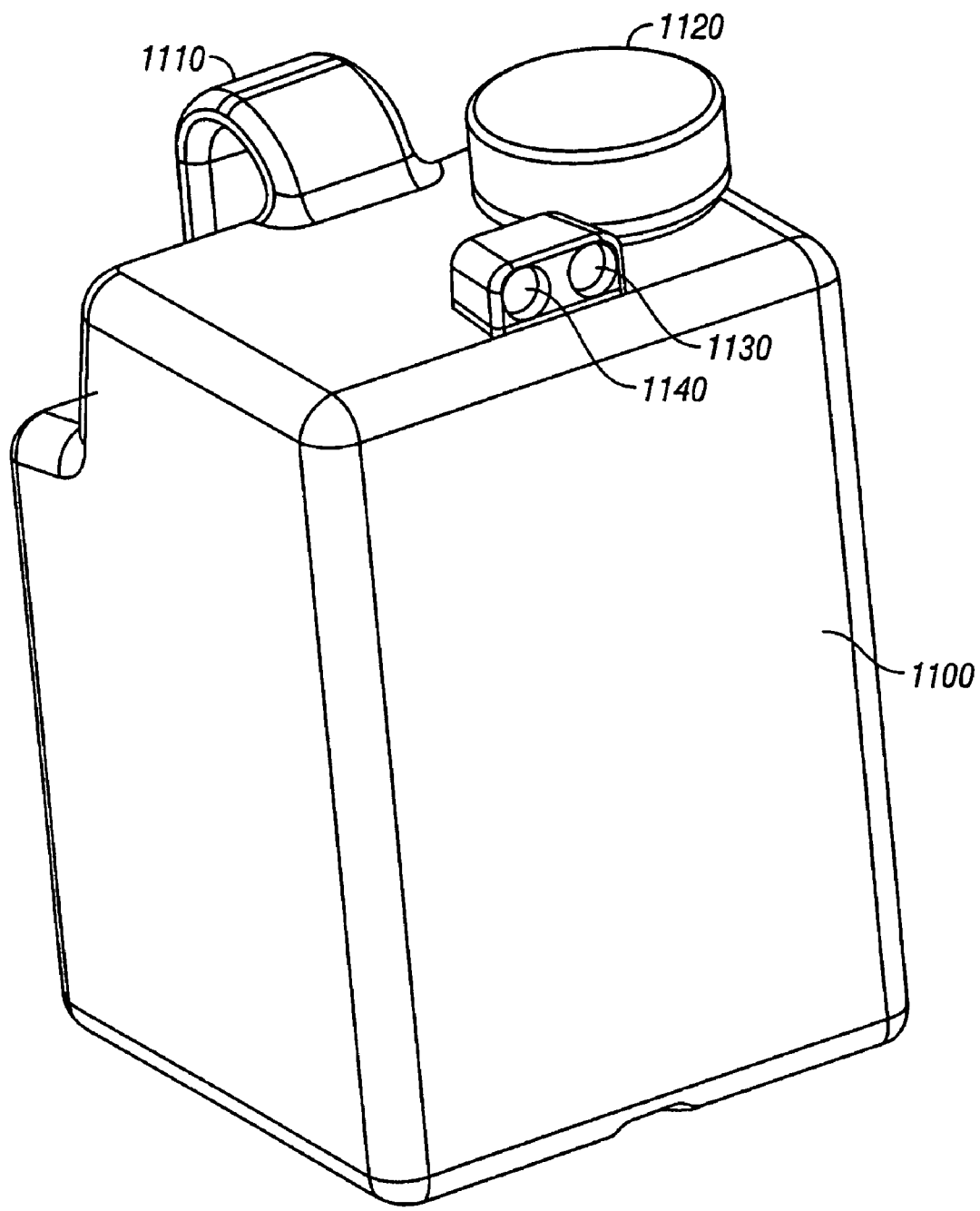
FIG. 11 is a perspective view of a supply/waste container in accordance with the present invention.
Figure 12:
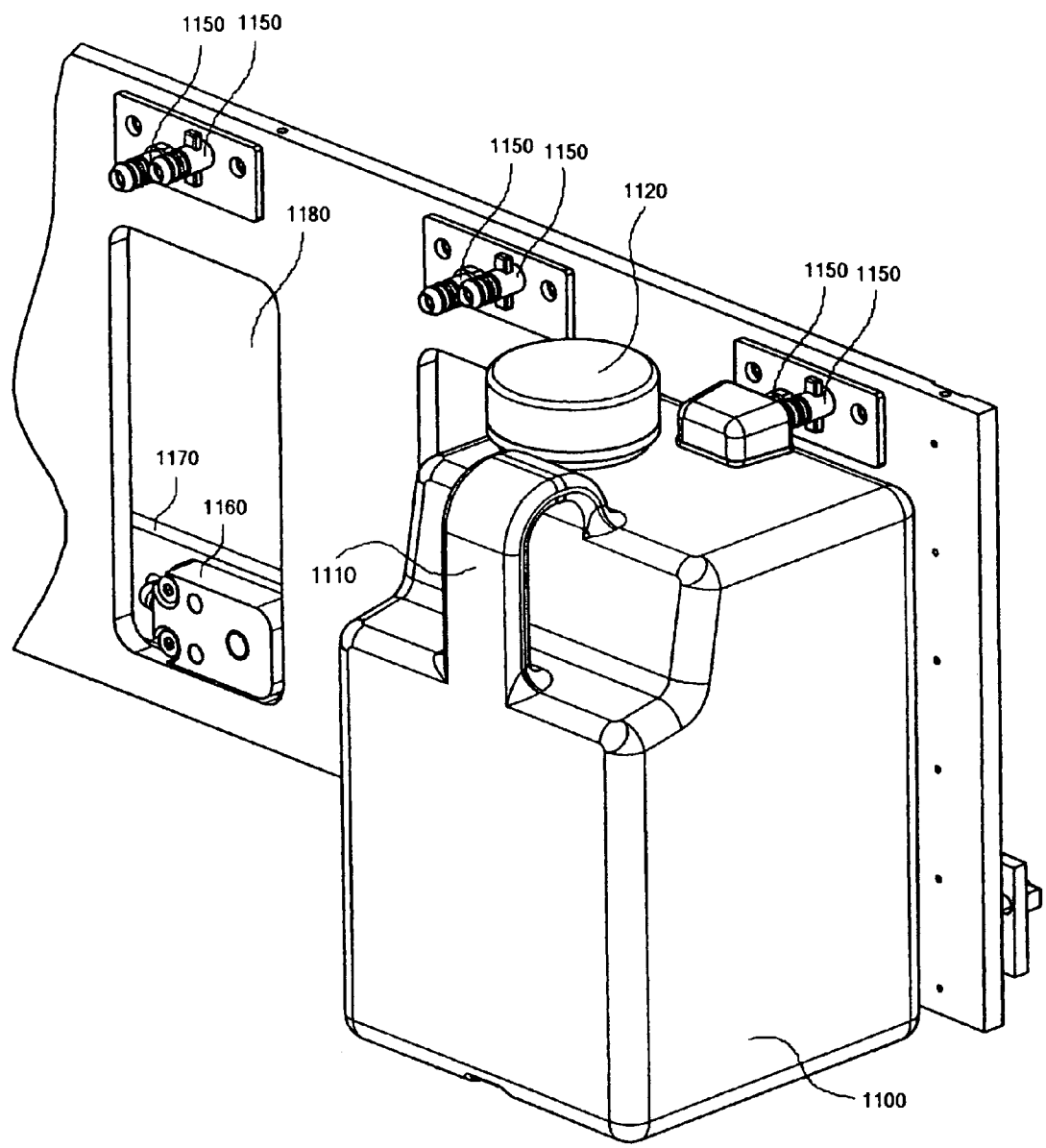
FIG. 12 is a perspective view of a supply/waste bottle coupled to a portion of a tissue processing system in accordance with the present invention.

FIGS. 11-12 illustrate a supply/waste bottle 1100 according to an embodiment of the present invention. The bottle 1100 may be of any desired configuration. Preferably, the bottle 1100 has a handle 1110 that facilitates transporting the bottle 1100. The bottle 1100 also has an access portion, or spout, that may be sealed using a conventional threaded cap 1120 or any other closure known in the art such as a snap-on cap. The bottle 1100 is also provided with a fluid port 1130 and a pressure port 1140. The fluid port 1130 may be used to supply or receive liquid as described above with respect to supply and waste bottles respectively. The fluid port may be any fluid port known in the art. For example the fluid port may be configured to receive a nipple that is part of a tissue processing system. In addition, a sealing feature may be included at the interface as part of bottle 1100 and/or as part of the tissue processing system. For example, a stopcock or self-sealing connector may be used.

The pressure port 1140 may be used to couple bottle 110 with a pressure pump or vacuum pump, as described above, to create a vacuum or pressure within the supply/waste bottle 1100 depending on whether the bottle is being used as a supply or waste bottle. The pressure port may be any fluid port known in the art. For example the fluid port may be configured to receive a nipple that is included in a tissue processing system. In addition, a sealing feature may be included at the interface as part of bottle 1100 and/or as part of the tissue processing system. For example, a stopcock or self-sealing connector may be used.

As shown in FIG. 12, the bottle 1100 may be connected to a supply or drain conduit of a tissue processing system by securing the fluid ports 1130 and the pressure ports 1140 to fittings 1150 provided on the tissue processing system. The fittings 1150 substantially securely attach the bottle 1100 to the supply and drain conduits leading to manifold assembly 500. According to an embodiment of the present invention, the fluid ports 1130 and pressure ports 1140 of the supply bottles and waste bottles are configured so that they may only mate with corresponding fittings 1150 provided for supply or waste bottles. For example, the fittings 1150 for a supply bottle may be of a different shape than the fittings 1150 for a waste bottle. In addition, or as an alternative, the pressure ports may be offset such that the pressure port on a supply bottle is positioned higher than the pressure port on a waste bottle Any type of distinguishing feature may be used that prevents a supply bottle from being attached to the system in a location designated for a waste bottle and vice versa.

One or more sensors 1160 may also be included, as shown in FIG. 12, to provide information regarding the fluid level of each of bottles 1100. In an embodiment, one sensor 1160 is movably mounted adjacent to each bottle 1100 so that it is able to move parallel to a vertical axis of bottle 1100. For example, sensor 1160 may be coupled to a translating sensor carrier 1170, such as a bar mounted on a vertical track. Sensor carrier 1170 may be mounted on tracks, or guides, included on a stationary portion of the system and it may be actuated in any way known in the art. For example, sensor carrier 1170 may be actuated by an electric motor, such as a stepper motor or constant reluctance motor, or it may be actuated hydraulically or pneumatically. As shown, each of sensors 1160 may be positioned in a respective aperture 1180 that extends through a portion of the system housing adjacent to each bottle location. Positioning sensor 1160 in aperture 1180 may reduce the distance between the sensor 1160 and a respective bottle. Preferably, one sensor 1160 corresponds to each bottle location and those sensors are coupled to a common sensor carrier. Such an embodiment may reduce sensor cost when compared to constructing a sensor array for each bottle. Furthermore, such a system may provide the ability to increase or decrease fluid level as desired without requiring an increase or decrease in sensors.

Positional feedback of sensor carrier 1170 and/or sensors 1160 is preferably also provided. For example, positional feedback may be provided by one or more proximity sensors which are triggered by movement of sensor carrier 1170 and/or sensors 1160. Other devices that may be used to provide positional feedback of sensor carrier 1170, sensors 1160 include electric or optical resolvers, linear variable displacement transducers (LVDT) or any other type of position sensor. In addition, in embodiments utilizing electric motors, motor driving software may be used to determine the position of sensor carrier 1170 and/or sensors 1160 for example by counting steps of a stepper motor. It shall also be appreciated that sensor 1160 may be any type of sensor known in the art that is capable of providing fluid level information to the system. Preferably, sensor 1160 is a capacitive sensor that is capable of determining the fluid level when sensor 1160 is positioned outside bottle 1100.

During operation of the tissue processing system, the system may require a determination of system status or material inventory which may include determining the fluid level of the bulk waste bottles and/or bulk supply bottles. In order to gather fluid level information, sensor carrier 1170 is moved in a vertical direction and sensor 1160 is used to determine the presence or absence of fluid in the respective bottle at incremental distances along the travel of carrier 1170. In an embodiment, sensor carrier 1170 may initially be positioned at a bottom position. Sensor carrier 1170 may then be moved incrementally upwards with sensor 1160 taking readings at each incremental position. In an embodiment, sensor readings are taken at two hundred and fifty five (255) incremental positions. Sensor 1160 may indicate a "triggered" status when it detects the presence of fluid at a position and a "non triggered" status when it does not detect the presence of fluid. The system may then determine the fluid level of a bottle by determining the locations between which status of sensor 1160 changed from "triggered" to "non triggered" or vice versa. It shall be appreciated that the sensor carrier and sensors may be driven in any direction and they may be moved in multiple directions while gathering a single reading. For example, the carrier may be moved downward from an upper initial position or the carrier may be moved between alternative upper and lower positions. It shall also be appreciated that the distance between each sensor reading need not remain constant. In particular, the carrier may be moved a relatively large distance between sensor readings until a change in sensor status is detected. Then the direction of travel may be reversed and sensor readings be taken a smaller distance apart until the sensor status changes. Multiple reversing steps may be included and the distance between readings may be reduced in each step. Such a technique be used to reduce the time required to determine the fluid level. It shall also be appreciated that the accuracy of the fluid level determination is dependent on the distance between incremental movements of sensor 1160 and may also be dependent on the type/kind of fluid contained in the bottle. As a result, as the distance between sensor readings is decreased the accuracy of the fluid level determination will increase.

Based on the fluid fill level determined for each bottle the system may initiate various procedures. Such procedures include the filling or emptying of one or more bottles, sending a signal to a user interface that a bottle requires replacement, pausing a procedure or shutting down the system. It shall be appreciated that the filling or emptying of the bulk bottles may be accomplished by replacing bottles or by utilizing larger bulk bottles and the manifold assembly described herein to initiate the desired flow between bottles. The larger bulk bottles may be included internal or external to the system.

Regardless of whether a vacuum or pressure is applied to the supply bottles 900 or the waste bottles 1000, fluid flow is caused by creating a pressure differential between the supply bottles 900 or waste bottles 1000 and the inlets 600 or outlets 610 of the manifold or bulk containers 910, 1020. The vacuum or pressure applied to the supply bottles 900 or the waste bottles 1000 creates a pressure gradient in a direction of desired fluid flow. The pressure may be monitored and is controlled between the fluid port 1130 and the pressure port 1140 to create a desired pressure gradient which enables the controller to control the valves to provide a controlled fluid flow.

The pressure differential between the inlets 600 and a reaction chamber provided in the automated reagent dispensing system may also induce fluid flow through the reaction chamber. Further pressure differentials can be generated by providing a negative pressure (or vacuum) at the outlets 610, inducing flow in the direction of the outlets 610. After the fluid(s) introduced into the reaction chamber have been within the chamber a desired amount of time, the fluid(s) remaining can be discharged via the outlets 610 in a similar fashion in which a negative pressure differential or vacuum is introduced via the outlets 610. Optionally, wash fluids may be introduced into the reaction chamber or pumped-in through inlets 600 to flush the reaction chamber as desired. Outlets 610 optionally include a filter (or plural small apertures) to screen or filter debris.

Figure 13:
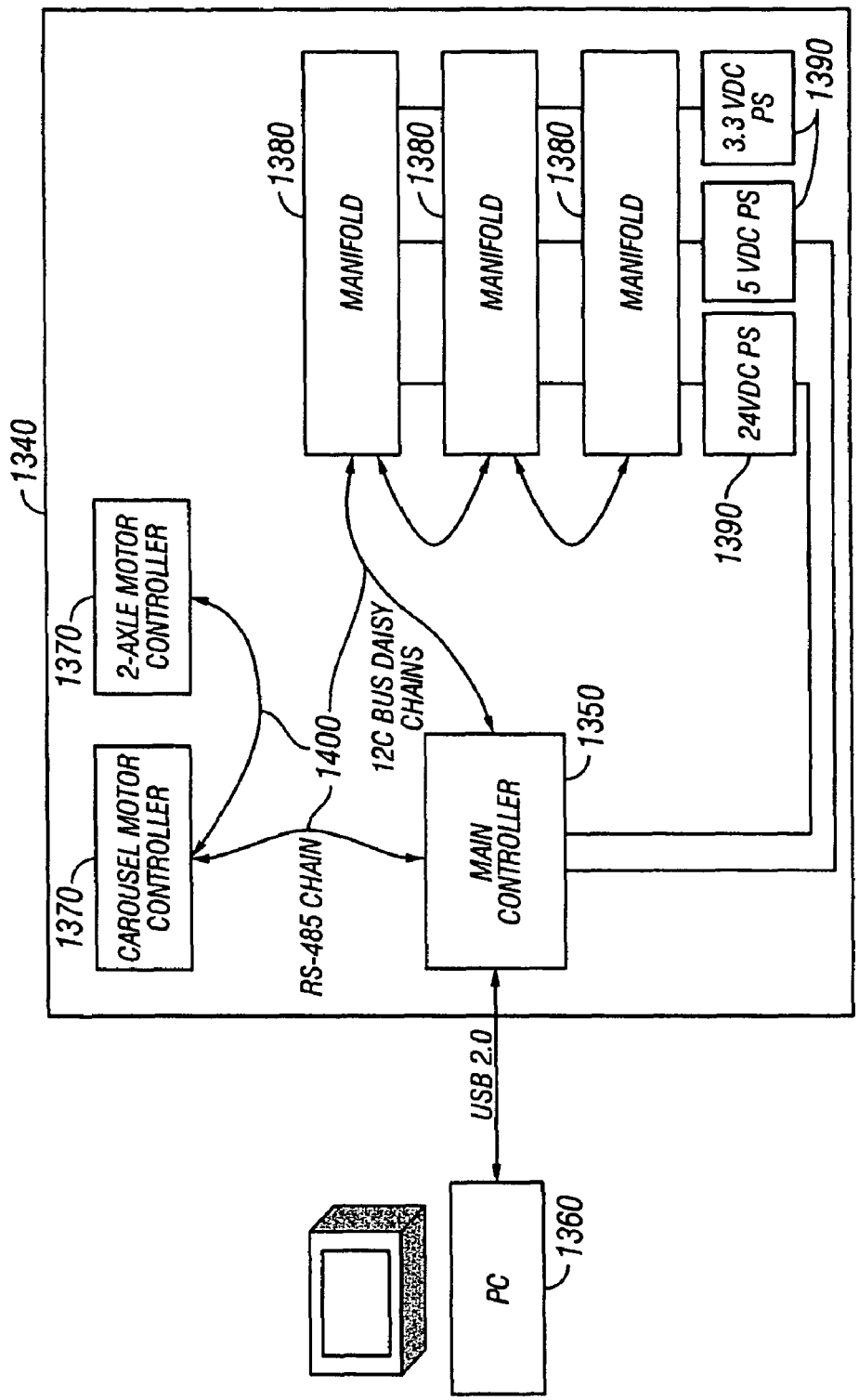
FIG. 13 is a block diagram of a tissue processing system in accordance with the present invention.

FIG. 13 is a block diagram of an automated tissue processing system 1340 according to an embodiment of the present invention. The system 1340 may include a main controller 1350. The main controller 1350 may be a central processing unit (CPU) or other controller. The main controller 1350 may be in communication with a personal computer 1360 or other device. The main controller 1350 may also be in communication with one or more peripheral controllers 1370. The controllers 1370 may be, for example, a carousel motor controller that controls rotational movement of the carousel (described above) provided in the automated tissue processing system 1340. Another controller 1370 may be a two-axle motor controller that controls horizontal and vertical movement of the carousel along a length and width of the automated tissue processing system 1340.

The main controller 1350 may also be in communication with one or more manifold assemblies 1380. The main controller 1350 may, for example, control the positions of valves provided on the manifold assemblies 1380 to create direct fluid paths between a tray and a supply or waste bottle as described above.

The manifold assemblies 1380 may be in communication with one or more power supplies 1390. The power supplies 1390 may provide power to the manifold assemblies 1380 such that the manifold assemblies may operate independently such as when the manifold assembly includes an onboard controller. The power supplies 1390 may provide different amounts of power. For example, the power supplies 1390 may include a twenty-four (24) volt (V) direct current (DC) power supply, a five (5) volt DC power supply, and a 3.3V DC power supply. Each power supply 1390 may be used to operate various portions of the manifold assemblies 1380. For example, different power supplies 1390 may be used to operate the valves, vacuum or pressure pumps and switches (described above).

An initialization procedure for an automated tissue processing system will now be described with reference to FIG. 14. The initialization procedure occurs after a start condition is detected (box 1410). A start condition may be, for example, closing a cover of the automated tissue processing system, receiving a start signal from a controller or other condition. If a start condition is not detected, the automated tissue processing system may continually check whether a start condition is detected until a start condition is received.

After detecting a start condition, an inventory procedure may be run as diagrammatically illustrated as box 1420 to determine the status of the reagent cartridges, supply bottles, specimen trays, etc. Upon completion of the inventory procedure, the automated reagent dispensing system may receive instruction sequences from a controller as diagrammatically illustrated as box 1430. The instruction sequences define one or more staining processes to be applied to the tissue samples mounted on the slides provided in the trays. The staining processes, as described above, identify which and how much of each reagent or other fluid is to be applied to each tissue sample and over what period of time.

Upon receiving the instruction sequences, staining protocols are run by the automated reagent dispensing system as diagrammatically illustrated as box 1440. While the staining protocols are run, the automated tissue processing system monitors whether an interrupt signal has been received. An interrupt signal may be caused by, for example, opening of the cover of the automated reagent dispensing system, a command received from the controller or another event. If an interrupt signal has been received, the automated reagent dispensing system stops processing as diagrammatically illustrated as box 1460. A determination is then made regarding whether a resume processing signal has been received. If a resume processing signal has not been received, the automated tissue processing system remains stopped (box 1460). If a resume processing signal has been received, however, the automated tissue processing system continues to run the staining protocols as diagrammatically shown as box 1440.

If an interrupt signal has not been received, a determination is made whether processing has been completed. Processing may include completing all staining protocols for each of the tissue samples provided in the automated tissue processing system. If the processing has not been completed, the automated tissue processing system continues to run the staining protocols as diagrammatically shown as box 1440. If a determination is made that processing is complete, a processing complete signal may be output to a controller (box 1490) and the automated reagent dispensing system stops processing as diagrammatically illustrated as box 1460.

Figure 15:
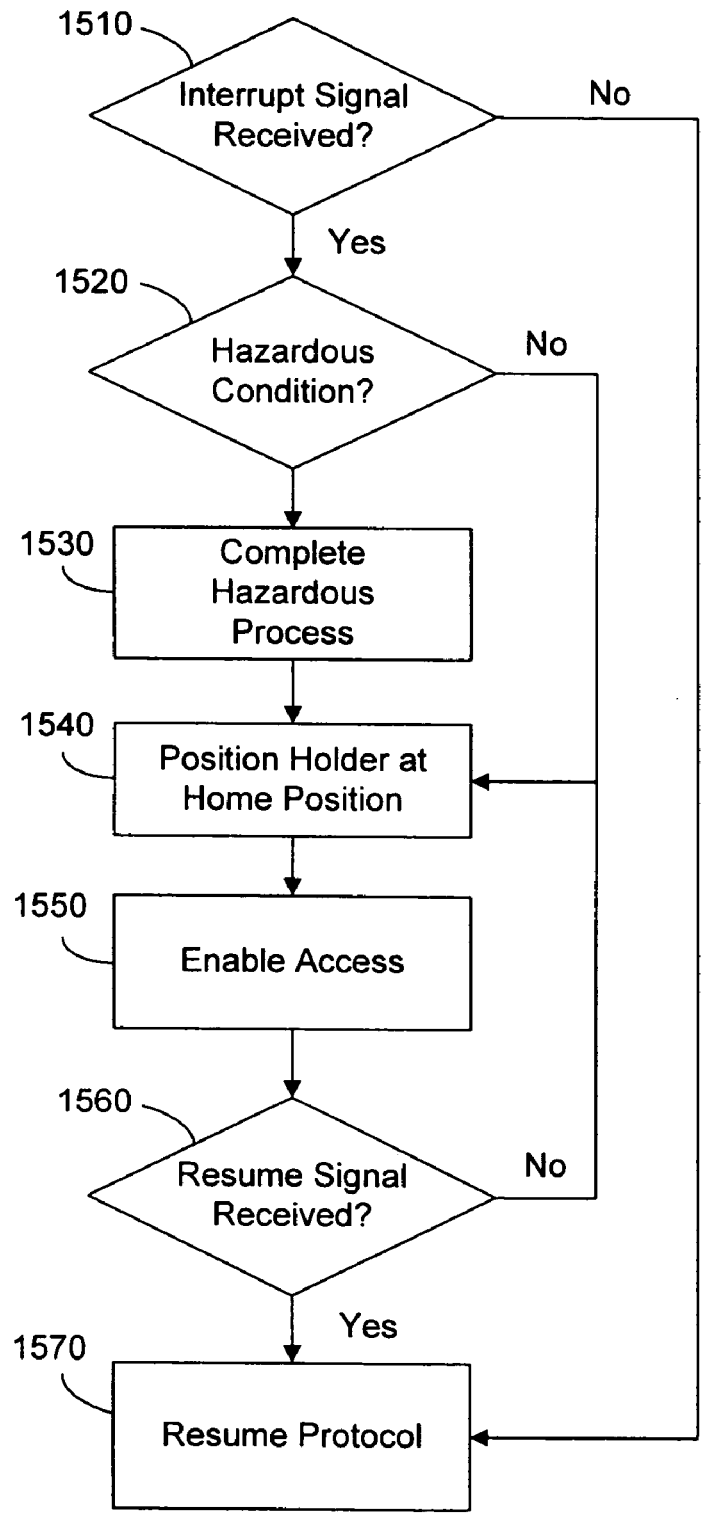
FIG. 15 is a flowchart depicting an interrupt event procedure of a reagent dispensing system in accordance with the present invention.

FIG. 15 illustrates, in further detail, an interrupt event procedure according to an embodiment of the present invention. A determination is made regarding whether an interrupt signal has been received (shown diagrammatically as box 1510). If an interrupt signal has been received, a determination is made regarding whether a hazardous condition exists as illustrated diagrammatically as box 1520. A hazardous condition may be, for example, that a reagent having a poisonous gas associated therewith has just been dispensed which may make a user ill if they are subjected to it. If a determination is made that a hazardous condition exists, the hazardous process may be completed as illustrated diagrammatically as box 1530. A carousel or other reagent cartridge holder may then be moved to a home position as shown diagrammatically as box 1540. The user is enabled access to an interior portion of the automated tissue processing system (box 1550). The user may be enabled access by, for example, unlocking a lock or other mechanism that prevents the cover of the automated tissue processing system from being opened.

The automated tissue processing system then determines whether a resume signal has been received as shown diagrammatically as box 1560. A resume signal may be caused by closing the cover or a command output by a controller as described above. If a resume signal has not been received, the automated tissue processing system continues to position the cartridge carousel or holder at a home position (box 1540). If, however, a resume signal has been received, the automated tissue processing system resumes the staining protocol(s) as illustrated diagrammatically as box 1570.

Figure 14:
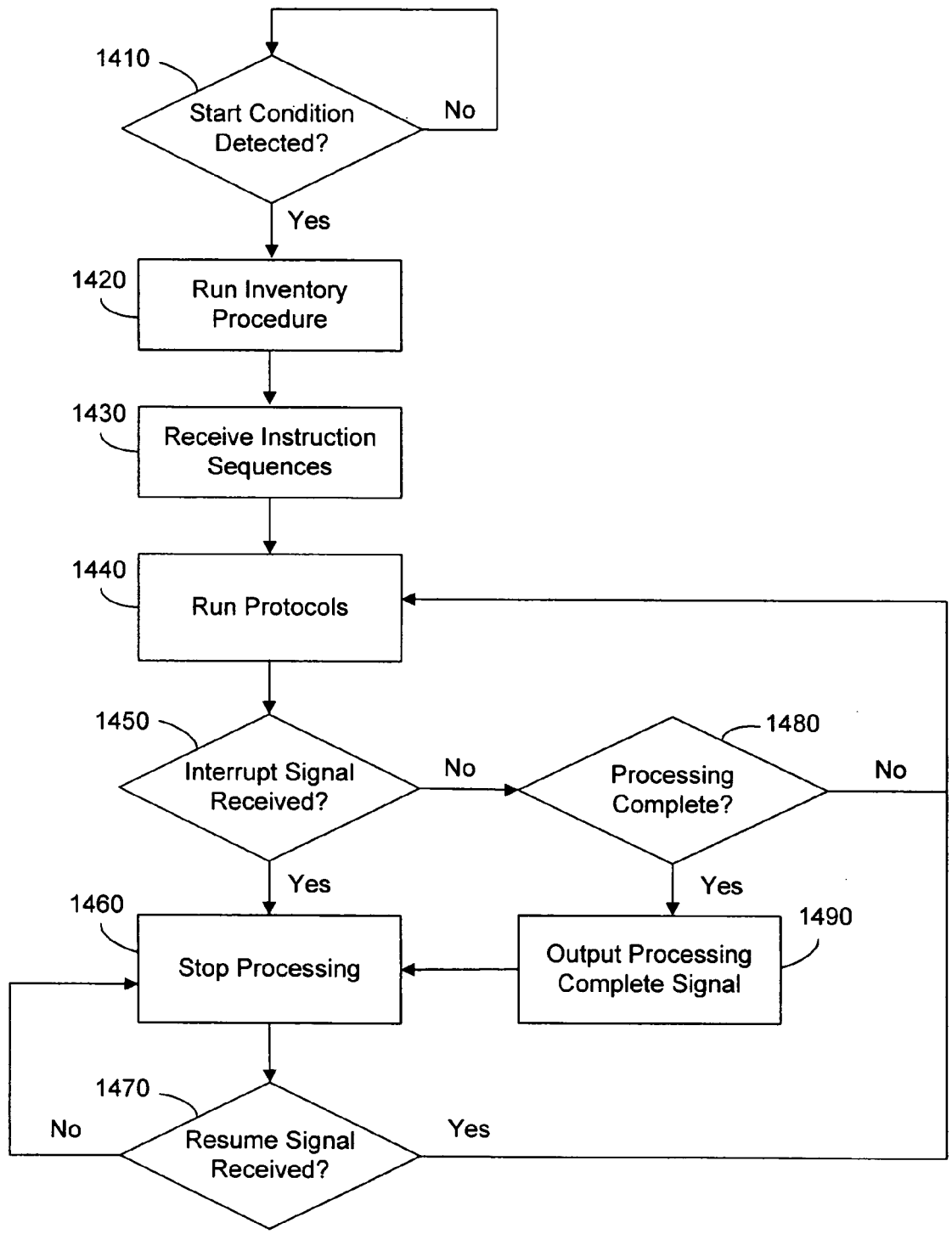
FIG. 14 is a flowchart depicting an initialization procedure of a reagent dispensing system in accordance with the present invention.
Figure 16:
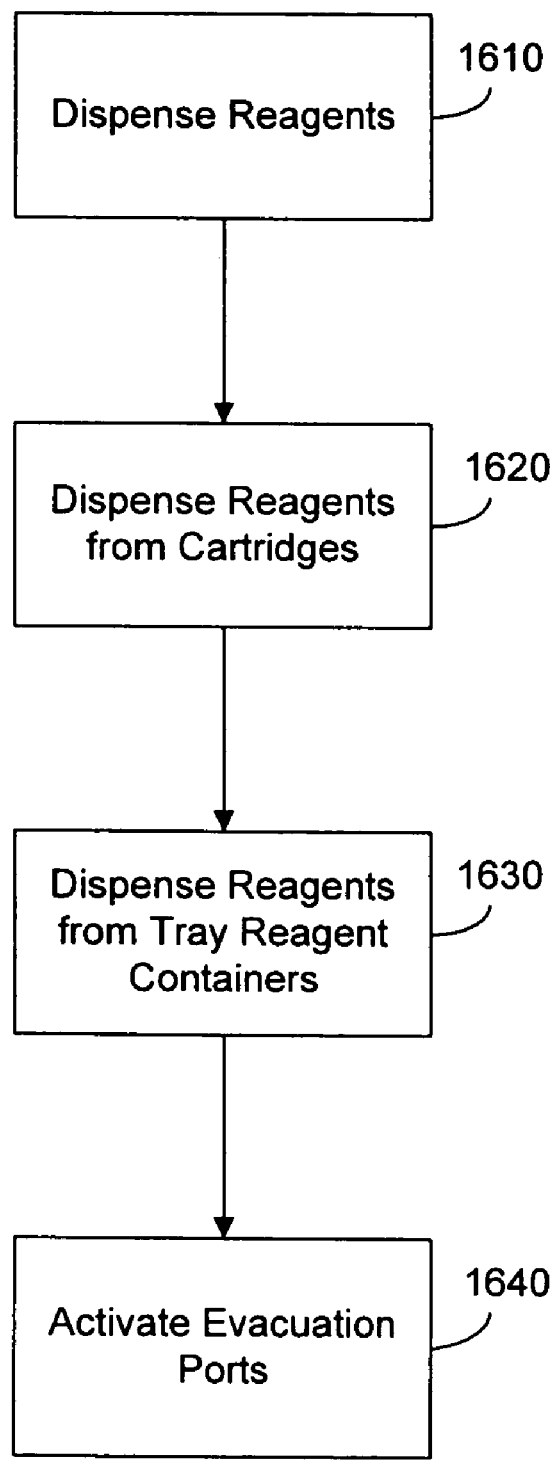
FIG. 16 is a flowchart depicting run protocols sub-steps of a reagent dispensing system in accordance with the present invention.

FIG. 16 illustrates sub-steps associated with a run protocols procedure illustrated diagrammatically as box 1440 in FIG. 14. A run protocols procedure includes dispensing reagents as shown diagrammatically as box 1610. The bulk containers may be used to supply the supply bottles with additional reagent. The bulk containers may be operated manually such that user intervention is required to transfer the reagent from the bulk container to the bottles. This may be done, for example, by operating a switch or other mechanism that causes the reagent to travel from the bulk container, through a supply line or other conduit, to the supply bottle. Alternatively, the automated tissue processing system may automatically fill the supply bottle. This may be performed after a scanning procedure is performed. For example, the scanning procedure may identify one or more bottles that contain a low volume of reagent require additional reagent. The automated tissue processing system may initiate filling of the bottles by causing reagent from an appropriate bulk container to travel to the bottle. This may be performed using a pump or other known mechanism.

The run protocols procedure also includes dispensing reagents from the cartridges as illustrated diagrammatically as box 1620. The reagent may be dispensed from the cartridge using, for example, a pump. The cartridges may be provided with a pump that is actuated by a solenoid. If a particular reagent is required to be dispensed, the automated tissue processing system actuates the solenoid associated with that cartridge by transmitting a signal to the solenoid. The solenoid pushes the pump and causes a predetermined amount of reagent to be dispensed from the cartridge. Preferably, the reagent is dispensed at desired times and according to a staining protocol. The automated tissue processing system may also dispense reagents from tray reagent containers as shown diagrammatically as box 1630.

Upon completion of a staining protocol, evacuation ports associated with the trays may be activated as illustrated diagrammatically as box 1640. The evacuation ports may be, for example, holes provided in the trays. A vacuum is applied to the tray that causes reagent located on the tray to be sucked into a waste conduit. According to one embodiment of the present invention, the waste may be divided into hazardous and non-hazardous waste with each going into a respective waste container.

Figure 17:
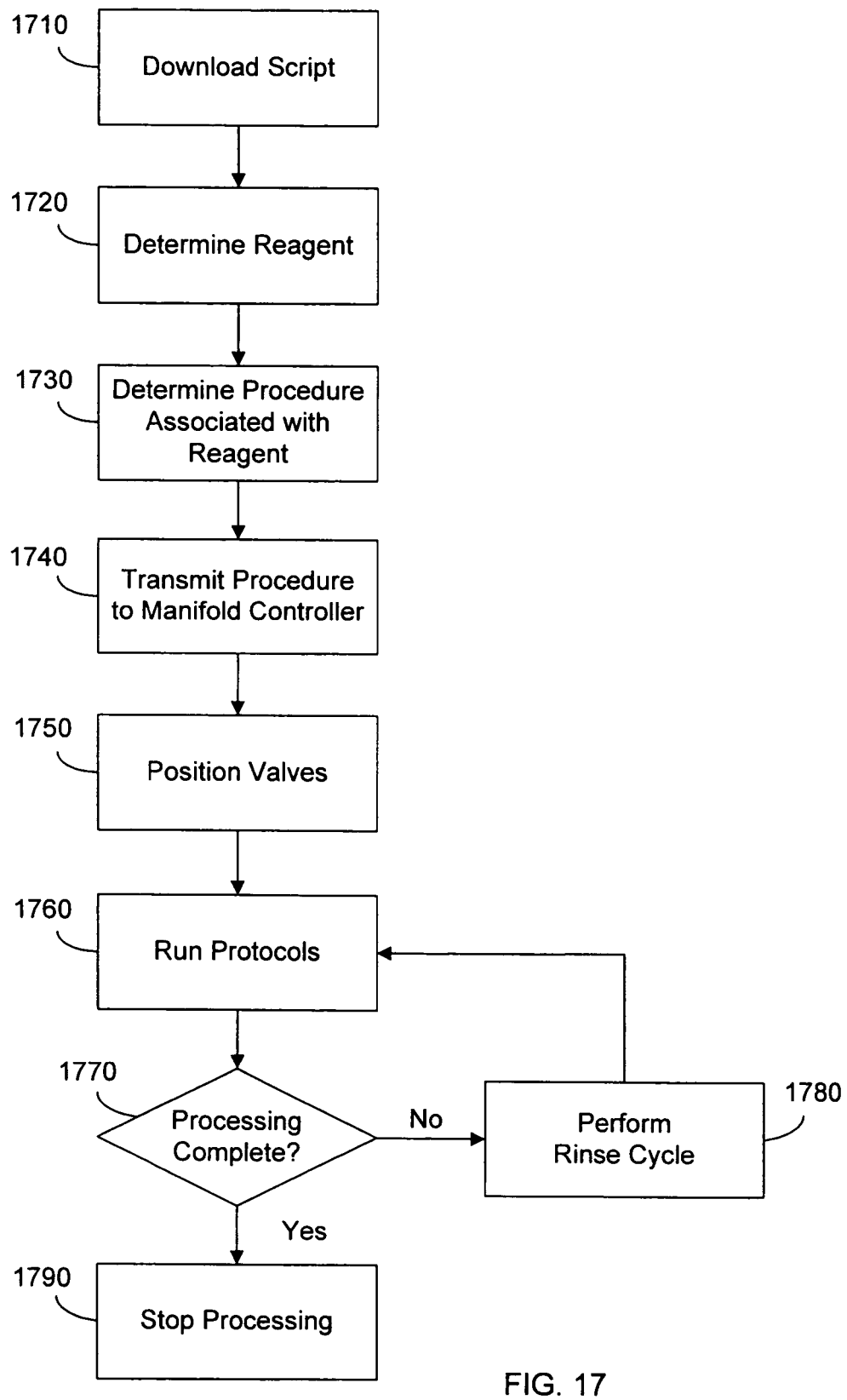
FIG. 17 is a flowchart depicting an overall procedure in accordance with the present invention.

FIG. 17 illustrates diagrammatically an overall procedure by an automated tissue processing system according to one embodiment of the invention. As an initial step, a script or processing program that defines the steps required to perform an automated staining procedure is downloaded from a controller. This step is illustrated diagrammatically as box 1710. The downloaded script may be based on information obtained by scanning an identifier associated with a slide. A primary reagent to be applied to the slide is determined as shown diagrammatically as box 1720. The primary reagent information may also be obtained from the identifier associated with the slide. One or more staining protocols to be applied to a particular slide are determined based on the primary reagent identified as illustrated diagrammatically as box 1730. The staining protocol(s) determined are then transmitted to a manifold controller as shown diagrammatically as box 1740. The manifold controller controls the carousel on which the cartridges are mounted and the dispensing of reagent from the cartridges. The manifold controller also controls the positions of the valves 640 (described above). Based on staining protocols to be run, the manifold controller determines which valves need to be in an opened position and which valves need to be in a closed position. The manifold controller then positions the valves in the positions determined (switching positions of any valve that may not already be in the position required) as diagrammatically illustrated as box 1750. Upon obtaining each of the necessary valves in the desired positions, the automated tissue processing system, as diagrammatically illustrated as box 1760 runs the protocol(s).

A determination is then made regarding whether the processing is complete as diagrammatically illustrated as box 1770. If a determination is made that the processing is not complete, a rinse cycle may be performed as diagrammatically illustrated as box 1780. The rinse cycle may be performed to drain reagents and/or other solutions introduced into the automated tissue processing system. The rinse cycle may include introducing water or other cleansing solution into the trays of the automated tissue processing system to wash the trays of the reagents or other solutions introduced. After completing the rinse cycle, the valves may again be positioned as required by an additional staining protocol to be run as diagrammatically illustrated as box 1750. If, however, a determination is made that processing is complete, the processing may stop as diagrammatically illustrated as box 1790.

Thus, it is seen that a manifold assembly for a tissue processing system and method is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. A manifold assembly for an automated tissue processing system comprising:
   a manifold including a surface and a pattern of fluid conduits extending therethrough; and
   a platen attached to the surface of the manifold, the platen having a substantially planar surface and defining a plurality of sample receiving portions each adapted to receive a slide retaining tray, wherein each of the plurality of sample receiving portions include an inlet and an outlet, the inlet and the outlet formed through separate portions of the platen defining the respective sample receiving portion, the inlet in fluid communication with at least one fluid conduit of the manifold and the outlet in fluid communication with at least one fluid conduit of the manifold.

2. The manifold assembly of claim 1 wherein the manifold is formed from two separate pieces of material.

3. The manifold assembly of claim 2 wherein the two separate pieces of material are mechanically etched to form complementing passageways and coupled such that the complementing passageways form the pattern of fluid conduits.

4. The manifold assembly of claim 2 wherein the material is a polymer.

5. The manifold assembly of claim 2 wherein the two pieces of material are mechanically fastened together.

6. The manifold assembly of claim 1 wherein the manifold is in fluid communication with at least one supply bottle and at least one waste bottle.

7. The manifold assembly of claim 6 further comprising a pressure pump in fluid communication with the at least one supply bottle.

8. The manifold assembly of claim 6 further comprising a vacuum pump in fluid communication with the at least one waste bottle.

9. The manifold assembly of claim 6 further comprising a fluid level sensor to monitor a fluid level of the at least one supply bottle.

10. The manifold assembly of claim 9 wherein the fluid level sensor is a first fluid level sensor and the manifold assembly further comprises a second fluid level sensor to monitor a fluid level of the at least one waste bottle.

11. The manifold assembly of claim 10 wherein the fluid level sensors are coupled to a common sensor carrier.

12. The manifold assembly of claim 11 wherein the sensor carrier is configured to translate parallel to a vertical axis of the supply bottle.

13. The manifold assembly of claim 1 further comprising an inlet port on a proximal end of the platen and an evacuation port on a distal end of the platen.

14. The manifold assembly of claim 1 further comprising a plurality of valves configured to control fluid flow through the fluid conduits.

15. The manifold assembly of claim 14 further comprising a valve controller coupled to the manifold.

16. The manifold assembly of claim 15 further comprising a drip frame coupled to the manifold between the manifold and the controller.

17. The manifold assembly of claim 1 further comprising at least one heater coupled to at least one of the sample receiving portions.

18. The manifold assembly of claim 1 further comprising a plurality of heaters coupled to the platen wherein each of the plurality of heaters is independently operated.

* * * * *